US007892739B2

(12) United States Patent
Vezenov

(10) Patent No.: US 7,892,739 B2
(45) Date of Patent: Feb. 22, 2011

(54) SYSTEMS, COMPOSITIONS AND METHODS FOR NUCLEIC ACID DETECTION

(75) Inventor: Dmitri Vezenov, Center Valley, PA (US)

(73) Assignee: Lehigh University, Bethlehem, PA (US)

( * ) Notice: Subject to any disclaimer, the term of this patent is extended or adjusted under 35 U.S.C. 154(b) by 168 days.

(21) Appl. No.: 12/057,251

(22) Filed: Mar. 27, 2008

(65) Prior Publication Data
US 2008/0286878 A1 Nov. 20, 2008

(51) Int. Cl.
*C12Q 1/68* (2006.01)
(52) U.S. Cl. .............................. 435/6; 436/94; 436/172
(58) Field of Classification Search ...................... None
See application file for complete search history.

(56) References Cited

U.S. PATENT DOCUMENTS

| | | | |
|---|---|---|---|
| 4,683,195 A | 7/1987 | Mullis et al. |
| 4,683,202 A | 7/1987 | Mullis |
| 4,889,818 A | 12/1989 | Gelfand et al. |
| 6,723,513 B2 | 4/2004 | Lexow |

OTHER PUBLICATIONS

Noy et al. "Stretching and breaking duplex DNA by chemical force microscopy". 1997. Chemistry and Biology. vol. 4, No. 7, pp. 519-527.*

Smith et al. "Overstretching B-DNA: The Elastic Response of Individual Double-Stranded and Single-Stranded DNA Molecules". 1996. Science. vol. 271. pp. 795-798.*
Bruchez et al. (1998) "Semiconductor Nanocrystals as Fluorescent Biological Labels," Science 281:2013-2016.
Chan et al. (1998) "Quantum Dot Bioconjugates for Ultrasensitive Nonisotopic Detection," *Science 281*:2016-2018.
Dabbousi et al. (1997) J. Phys. Chem. B 101:9463-9475.
Gerion et al. (2001) J. Phys. Chem. B 105:8861-8871.
Gao et al. (2003) J. Am. Chem. Soc. 125:3901-3909.
Hines et al. (1996) J. Phys. Chem. 100:468-471.
Ju et al. (2006) "Four-color DNA sequencing by synthesis using cleavable fluorescent nucleotide reversible terminators," Proc. Natl. Acad. Sci. 103:19635-19640.
Murray et al. (1993) J. Am. Chem. Soc. 115:8706-8715.
Rogach et al. (2000) Chem. Mater. 12:2676-2685.
Seliger et al. (1991) Nucleosides and Nucleotides 10:303-306.
Seo et al. (2004) "Photocleavable fluorescent nucleotides for DNA sequencing on a chip constructed by site-specific coupling chemistry," Proc. Natl. Acad. Sci. 101:5488-5493.
Zhang (2003) Journal of Nanoparticle Research 5:323-332.

* cited by examiner

*Primary Examiner*—Yelena G Gakh
*Assistant Examiner*—David Weisz
(74) *Attorney, Agent, or Firm*—Medlen & Carroll, LLP

(57) ABSTRACT

The invention relates to stretch measurements of nucleic acids and correlating those measurements to the extent of double- and single-stranded content of a nucleic acid of interest, and to compositions, systems, and devices related thereto. In preferred embodiments, one performs the stretch or elasticity measurements under conditions such that one can determine a nucleic acid sequence or the presence of an oligonucleotide in a sample.

15 Claims, 14 Drawing Sheets

SYSTEMS, COMPOSITIONS AND METHODS FOR NUCLEIC ACID DETECTION

FIELD OF INVENTION

The invention relates to stretch measurements of nucleic acids and correlating those measurements to the extent of double- and single-stranded content of a nucleic acid of interest, and to compositions, systems, and devices related thereto. In preferred embodiments, one performs the stretch or elasticity measurements under conditions such that one can determine a nucleic acid sequence or the presence of an oligonucleotide in a sample.

BACKGROUND OF INVENTION

Nucleic acid sequencing is one of the most important technologies in bioscience today. Whole-genome approaches and human expressed sequence tag (EST) sequencing have started to exert profound influences on biology and medicine. New applications, such as population-based biodiversity projects and genotyping using single-nucleotide polymorphism (a "brute-force" approach), make such efforts even more urgent. Thus, there is a need for simple and robust methods for sequencing nucleotide sequences suitable for routine diagnostic applications.

SUMMARY OF INVENTION

The invention relates to stretch measurements of nucleic acids and correlating those measurements to the extent of double- and single-stranded content of a nucleic acid of interest, and to compositions, systems, and devices related thereto. In preferred embodiments, one performs the stretch or elasticity measurements under conditions such that one can determine a nucleic acid sequence or the presence of an oligonucleotide in a sample.

The invention relates to stretch measurements of nucleic acids and correlating those measurements to the extent of double- and single-stranded content of a nucleic acid of interest, and to compositions, systems, and devices related thereto. In preferred embodiments, one performs the stretch or elasticity measurements under conditions such that one can determine a nucleic acid sequence or the presence of an oligonucleotide in a sample.

In some embodiments, the invention provides a system for stretching a nucleic acid. The system comprises a substrate that supports a nucleic acid conjugate. The conjugate comprises a nucleotide sequence having a first end and a second end, the first end being immobilized on (i.e., attached to) the substrate. The conjugate also comprises a distance marker and a molecular handle. The second end of the nucleotide sequence is linked to the distance marker and to the molecular handle.

Another element of the system is an instrument configured to exert force on the molecular handle, to measure distances of the distance marker from the substrate, and to measure forces on the molecular handle during stretching.

In some embodiments, the molecular handle may be a ligand such as biotin, in other embodiments, a magnetic particle serves as a molecular handle. The distance marker is preferably a particle of a size between $1 \times 10^{-9}$ m to $10^{-4}$ m, and may comprise an inorganic oxide, including without limitation silica or titania, an organic polymer such as polystyrene, or a composite material.

In some embodiments, the distance marker comprises quantum dots dispersed in or on it as a luminescent moiety. Other luminescent moieties are within the scope of the invention, as are dielectric spheres or metallic particles.

In some embodiments, the instrumental element of the system may be equipped with a proximity probe that interacts with the molecular handle. In some embodiments, a cantilever tip of the type used in atomic force microscopy may serve as a proximity probe. The proximity probe may include a receptor such as streptavidin to promote interaction with the molecular handle.

In some embodiments, the instrument interacts with the molecular handle by means of a magnet. In other embodiments, the molecular handle is manipulated by an optical trap fashioned into the instrument.

In some embodiments, the invention provides a method of determining the presence of an oligonucleotide in a sample. According to the method a sample suspected of containing an oligonucleotide (of known or unknown nucleotide sequence) is contacted with a nucleic acid conjugate comprising a nucleic acid, preferably single-stranded, having a first end and a second end and further comprising a nucleotide sequence that is complementary to the suspected oligonucleotide. The first end is immobilized on a substrate. In addition to the nucleic acid, the conjugate comprises a distance marker and a molecular handle, both of which are attached to the second end of the nucleic acid.

Preferably, the method employs an instrument configured to exert (and measure) force on the molecular handle. The instrument is used to move the molecular handle such that the nucleic acid is stretched and to measure the distance from the substrate the distance marker traverses to establish a first distance, and the forces applied.

According to the method, the sample is caused to contact the nucleic acid in the conjugate under conditions such that the oligonucleotide in the sample hybridizes to the nucleic acid to create a nucleic acid conjugate such that at least a portion of the nucleic acid is a double-stranded nucleic acid. A second distance (and the forces applied) is measured by moving the molecular handle with the instrument under conditions such that the double-stranded nucleic acid is stretched. The correlation of the two distances determines the presence of the oligonucleotide.

In one embodiment, the present invention contemplates a nucleic acid conjugate. The conjugate, in this embodiment, comprises a single-stranded nucleic acid having a first end and a second end wherein said first end is immobilized on a substrate, which may be transparent. The conjugate further comprises a nucleotide sequence complementary to a portion of the single-stranded nucleic acid, and hybridized thereto. The conjugate further comprises a distance marker and a molecular handle, both of which are linked to the second end of the single-stranded nucleic acid element of the conjugate. The distance marker may be a luminescent moiety such as a quantum dot, a dielectric sphere or a metallic particle. The molecular handle may be a ligand, a magnetic particle, or any particle of a size between $0.1 \times 10^{-9}$ m to $10^{-4}$ m.

The invention is further embodied in a method that comprises providing a system for stretching a nucleic acid, the system comprising a substrate, a nucleic acid conjugate, and an instrument. The conjugate comprises a single-stranded nucleic acid having a first end and a second end, the first end being immobilized on the substrate. The conjugate further comprises a nucleotide sequence complementary to the single-stranded nucleic acid and hybridized thereto to create a partially double-stranded nucleic acid, wherein the complementary sequence has a free 3' end. The conjugate further comprises a distance marker, and a molecular handle. The second end of single-stranded nucleic acid element of the conjugate is linked to the distance marker and molecular handle. An instrument configured to exert force on the molecular handle further comprises the system. A sample comprising a nucleotide, preferably of known structure, is also provided.

According to one embodiment of the method, the instrument is employed to move the molecular handle under conditions such that the partially double-stranded nucleic acid is stretched, a first distance of said distance marker from the substrate is measured (optionally as a function of the forces applied), the sample and the conjugate are contacted under conditions such that the nucleotide becomes ligated to the free 3' end of the complementary sequence to create an extended double-stranded nucleic acid (extended by one nucleotide), the molecular handle is moved under conditions that stretch the extended nucleic acid, a second distance of the distance marker from the substrate is measured (optionally as a function of the forces applied), and the first and second distances are correlated to determine the presence of the complementary nucleotide. The distance measurements and ligation steps may be repeated until the entire sequence of the nucleic acid is determined. Thermal noise that may be acquired during the measurements may be removed by averaging data or by averaging differences between sets of force-length data. Further statistical confidence may be reached by fitting averaged or individual force-length measurements to a model of a stretched polymer chain.

Again, the distance marker may be a luminescent moiety such as a quantum dot, a dielectric sphere or a metallic particle; the molecular handle may be a ligand (e.g., biotin) a magnetic particle, or any particle (e.g., an inorganic oxide, an organic polymer or a composite material) of a size between $0.1 \times 10^{-9}$ m to $10^{-4}$ m. The distance marker may have quantum dots dispersed in or on it as a luminescent moiety. Other luminescent moieties are within the scope of the invention, as are dielectric spheres or metallic particles.

Further, the instrumental element of the system may be equipped with a proximity probe that interacts with the molecular handle. In some embodiments, a cantilever tip of the type used in atomic force microscopy may serve as a proximity probe. The proximity probe may include a receptor such as streptavidin to promote interaction with the molecular handle. Alternatively, the instrument may be configured to interact with the molecular handle by means of a magnet. In other embodiments, the molecular handle is manipulated by an optical trap fashioned into the instrument.

In some embodiments, the systems and methods that embody the invention comprise, in addition to a nucleic acid conjugate and an instrument for stretching a nucleic acid and measuring the distance traversed and the forces applied, a device comprising a plurality of channels, each configured to direct a liquid to the nucleic acid conjugate. In some embodiments, the channels have a width less than about a millimeter and, preferably, less than a micrometer. In some embodiments, the liquid comprises a nucleotide or an oligonucleotide.

In some embodiments, the systems and methods that embody the invention provide for processing a plurality of samples, wherein each sample comprises an oligonucleotide containing at least six contiguous nucleotides, and wherein the samples collectively contain all possible nucleotide sequences in a predetermined set of nucleotides. In these embodiments, force-strength measurements are made for a single-stranded nucleic acid, one of the samples is contacted with a nucleic acid conjugate of the system under hybridizing conditions for the oligonucleotide in that sample, force-length measurements are made for the hybridized nucleic acid, another of the samples is contacted with the single-stranded nucleic acid or, alternatively, with the hybridized nucleic acid, force-length measurements are again made. Differences between measurements are correlated to determine a presence of a complementary oligonucleotide in the nucleic acid and the process is repeated with other samples to identify all partial sequences in the single-stranded nucleic acid that hybridize with complementary oligonucleotides in the samples.

In some embodiments, the invention relates to a system for stretching a nucleic acid comprising: a) a substrate comprising, a nucleotide sequence conjugate comprising a distance marker, and a molecular handle, wherein a first end of said nucleotide sequence is immobilized to said substrate, and wherein a second end of said nucleotide sequence is linked to said distance marker and molecular handle, b) an instrument configured to exert force on said molecular handle and measure the distance of said marker from said substrate. In further embodiments, said molecular handle is selected from the group consisting of a ligand, magnetic particle, and particle of a size between $1 \times 10^{-9}$ m to $10^{-4}$ m. In further embodiments, said ligand is biotin. In further embodiments, said particle is an inorganic oxide, an organic polymer, or composite particle. In further embodiments, said inorganic oxide is silica or titania. In further embodiments, said organic polymer is polystyrene. In further embodiments, said composite particle is a polystyrene dispersed with quantum dots or silica dispersed with quantum dots. In further embodiments, said distance marker is selected from the group consisting of a luminescent moiety, a dielectric sphere, and a metallic particle. In further embodiments, said luminescent moiety comprises a quantum dot. In further embodiments, said instrument comprises a proximity probe comprising a receptor. In further embodiments, said probe is a cantilever tip. In further embodiments, said receptor is streptavidin. In further embodiments, said instrument comprises a magnet. In further embodiments, said instrument is configured to create an optical trap.

In some embodiments, the invention relates to a method of determining the presence of an oligonucleotide in a sample comprising: a) providing, i) a sample suspected of containing an oligonucleotide; ii) a substrate comprising a nucleic acid conjugate comprising a single-stranded portion complimentary to said oligonucleotide a distance marker, and a molecular handle; wherein a first end of said single-strand is immobilized on a substrate and wherein a second end of said single-strand is linked to said distance marker and molecular handle; iii) an instrument configured to exert force on said molecular handle; b) mixing said sample and said substrate under conditions such that said oligonucleotide hybridizes to said nucleic acid conjugate; c) moving said molecular handle with said instrument under conditions such that the nucleic acid is stretched; d) measuring a distance of said distance marker from said substrate; and f) correlating said measured distance to a presence of said oligonucleotide in said sample.

In further embodiments, the invention relates to a substrate comprising, a nucleic acid conjugate comprising: a single-stranded portion, a double-stranded portion, a distance marker, and a molecular handle wherein a first end of said single-strand is immobilized on a substrate and wherein a second end of said single-strand is linked to said distance marker and molecular handle. In further embodiments, said distance marker is selected from the group consisting of a luminescent moiety, dielectric spheres, and metallic particles. In further embodiments, said luminescent moiety is a quantum dot. In further embodiments, said molecular handle is selected from the group consisting of a ligand, magnetic particle, and particle of a size between $0.1 \times 10^{-9}$ m to $10^{-4}$ m. In further embodiments, said substrate comprises a transparent surface.

In some embodiments, the invention relates to a method comprising: A) providing i) a system for stretching a nucleic acid comprising a) a substrate comprising, a nucleic acid conjugate comprising: a) a single-stranded portion, b) a double-stranded portion comprising a free 3' end, c) a distance marker, and d) a molecular handle, wherein a first end of said single-strand is immobilized on a substrate and wherein a second end of said single-strand is linked to said distance marker and molecular handle; b) an instrument configured to exert force on said molecular handle and measure the distance and force of said distance marker from said substrate ii) a sample comprising a nucleotide; B) mixing said sample and system under conditions such that said nucleotide is ligated to said free 3' end, C) moving said molecular handle with said instrument under conditions such that the nucleic acid is stretched, D) measuring a distance of said distance marker from said substrate and, F) correlating said distance to the presence of a complimentary nucleotide in said nucleic acid. In further embodiment, the method further comprises repeating steps B-D to determine the sequence of said nucleic acid. In further embodiments, said distance marker is selected from the group consisting of a luminescent moiety, dielectric spheres, and metallic particles. In further embodiments, said luminescent moiety is a quantum dot. In further embodiments, said molecular handle is selected from the group consisting of a ligand, magnetic particle, and particle of a size between $1 \times 10^{-9}$ m to $10^{-4}$ m. In further embodiments, said instrument comprises a proximity probe comprising a receptor. In further embodiments, said probe is a cantilever tip. In further embodiments, said receptor is streptavidin. In further embodiments, said instrument is a magnet. In further embodiments, said instrument is configured to create an optical trap.

In further embodiments, the invention relates to a method comprising: A) providing i) a system for stretching a nucleic acid comprising a) a substrate comprising, a nucleic acid conjugate comprising a single-stranded portion, a double-stranded portion comprising a free 3' end, a distance marker, and a molecular handle, wherein a first end of said single-strand is immobilized on a substrate and wherein a second end of said single-strand is linked to said distance marker and molecular handle; b) an instrument configured to exert force on said molecular handle and measure said force applied to said molecular handle and measure said a distance of said distance marker from said substrate; ii) a sample comprising a nucleotide; B) mixing said sample and system under conditions such that said nucleotide is ligated to said free 3' end, C) moving said molecular handle with said instrument under conditions such that the nucleic acid is stretched, D) generating a plurality of force and length data and, F) correlating said data to the presence of a complimentary nucleotide in said nucleic acid. In further embodiments, the method further comprises the step of calculating a noise average of said data measurements. In further embodiments, the method further comprises the step of fitting said thermal noise average to a polymer model. In further embodiments, the method further comprises the step of removing the thermal noise by averaging said data measurements or by averaging differences between two sets of said force-length data. In further embodiments, the method further comprises the step of removing the effect of said noise by fitting the averaged or individual force-length data measurements to a model of a stretched polymer chain.

In some embodiments, the invention relates to a system comprising: a) a device comprising a plurality of channels configured to direct a liquid to a substrate, said substrate comprising, a nucleic acid conjugate comprising: a single-stranded portion, a distance marker, and a molecular handle, wherein a first end of said single-strand is immobilized to said substrate, and wherein a second end of said single-strand is linked to said distance marker and molecular handle; b) an instrument configured to exert force on said molecular handle. In further embodiments, said channels have a width that is less that 1 millimeter or less than 1 micrometer. In further embodiments, said liquid comprises a nucleotide.

In some embodiments, the invention relates to a method comprising: a) providing i) a plurality of oligonucleotides containing 6 (six) or more contiguous nucleotides ii) a substrate comprising a nucleic acid conjugate comprising a single-stranded portion complimentary to one of said plurality of oligonucleotide, a distance marker, and a molecular handle; wherein a first end of said single-strand is immobilized to the substrate and wherein a second end of said single-strand is linked to said distance marker and molecular handle; iii) an instrument configured to exert force on said molecular handle; b) mixing one of said oligonucleotide and said substrate under conditions such that said oligonucleotide hybridizes to said nucleic acid conjugate; c) moving said molecular handle with said instrument under conditions such that the nucleic acid is stretched; d) measuring a distance of said distance marker from said substrate; and f) correlating said measured distance to a presence of said complimentary oligonucleotide sequence in said nucleic acid.

In additional embodiments, the invention relates to a method of determining the presence of an oligonucleotide in a sample comprising: a) providing i) a sample suspected of containing an oligonucleotide; ii) a substrate comprising a nucleic acid conjugate comprising a single-stranded portion complimentary to said oligonucleotide, a distance marker, and a molecular handle; wherein a first end of said single-strand is immobilized to the substrate and wherein a second end of said single-strand is linked to said distance marker and molecular handle; iii) an instrument configured to exert force on said molecular handle; b) mixing said sample and substrate under conditions such that said oligonucleotide hybridizes to said nucleic acid conjugate; c) moving said molecular handle with said instrument under conditions such that the nucleic acid is stretched; d) measuring a distance of said distance marker from said substrate at varying or constant force or measuring the elastic response of said distance marker; and f) correlating said measured distance as a function of applied force, i.e., elastic response, to a presence of said oligonucleotide in said sample by detection of bonding of said oligonucleotide to the nucleic acid.

In further embodiments, the invention relates to a method of sequencing a nucleic acid comprising: a) providing i) a plurality of oligonucleotides containing 2 (two), 3 (three), 4 (four), 5 (five), 6 (six), 7 (seven), or 8 (eight) or more contiguous nucleotides; ii) a substrate comprising a nucleic acid conjugate comprising a single-stranded portion complimentary to one of said plurality of oligonucleotide, a distance marker, and a molecular handle; wherein a first end of said single-strand is immobilized to the substrate and wherein a second end of said single-strand is linked to said distance marker and molecular handle; iii) an instrument configured to exert force on said molecular handle; b) mixing one of said oligonucleotide and said substrate under conditions such that said oligonucleotide hybridizes to said nucleic acid conjugate; c) moving said molecular handle with said instrument under conditions such that the nucleic acid is stretched; d) measuring a distance of said distance marker from said substrate at varying or constant force or measuring the elastic response of said distance marker; and f) correlating said measured distance as a function of applied force, i.e., elastic response, to a presence of said complimentary oligonucleotide sequence in said nucleic acid.

In some embodiments, the invention relates to a substrate comprising, a nucleic acid conjugate comprising: a single-stranded portion, a double-stranded portion, a distance marker, and a molecular handle. In further embodiments, said distance marker is selected from the group consisting of a luminescent moiety, dielectric spheres, and metallic particles. In further embodiments, said luminescent moiety is a quantum dot. In further embodiments, said molecular handle is selected from the group consisting of a ligand, magnetic particle, and particle of a size between $1\times10^{-9}$ m to $10^{-4}$ m. In further embodiments, said substrate comprises a transparent surface.

In additional embodiments, the invention relates to a method comprising: A) providing i) a system for stretching a nucleic acid comprising a) a substrate comprising, a nucleic acid conjugate comprising a single-stranded portion, a double-stranded portion comprising a free 3' end, a distance marker, and a molecular handle, b) an instrument configured to exert force on said molecular handle, ii) a sample comprising a nucleotide; B) mixing said sample and system under conditions such that said nucleotide is ligated to said free 3' end C) moving said molecular handle with said instrument under conditions such that the nucleic acid is stretched, D) measuring a distance of said distance marker from said substrate with a changing force and, F) correlating said distance to the presence of a complimentary nucleotide in said nucleic acid. Additional embodiments further comprise repeating steps B through D to determine the sequence of said nucleic acid by cycling through nucleotides of different type and inferring the nucleotide sequence because of the corresponding Watson-Crick base pairing rules. In further embodiments, said distance marker is selected from the group consisting of a luminescent moiety, dielectric spheres, and metallic particles. In further embodiments, said luminescent moiety is a quantum dot. In further embodiments, said molecular handle is selected from the group consisting of a ligand, magnetic particle, and particle of a size between $0.1\times10^{-9}$ m to $10^{-4}$ m. In further embodiments, said instrument comprises a proximity probe comprising a receptor. In further embodiments, said probe is a cantilever tip. In further embodiments, said receptor is streptavidin. In further embodiments, said instrument is a magnet. In further embodiments, said instrument is configured to create an optical trap.

In some embodiments, the invention relates to a method of measuring a hybridization of a nucleic acid comprising; a) providing: i) a first single-stranded nucleic acid, i) a second single-stranded nucleic acid comprising one or more nucleotides in a predetermined sequence, iii) a solid support, and iv) a force spectrometer; b) immobilizing said first nucleic acid to said solid support; c) immobilizing said second nucleic acid to a tip of said force spectrometer; d) slidably contacting said first nucleic acid with said second nucleic acid under hybridizing conditions; and e) measuring forces between said first and second nucleic acids.

In additional embodiments, the invention relates to a method of measuring a degree of hybridization of a complimentary nucleotide to a nucleic acid sequence comprising; a) providing: i) a single-stranded nucleic acid sequence, ii) a nucleotide sequence wherein a portion of the nucleotide sequence is complimentary to said nucleic acid sequence, iii) a solid support, and iv) a force spectrometer; b) immobilizing said first nucleic acid to said solid support; c) measuring a first elasticity of said first nucleic acid sequence using said force spectrometer; d) mixing said second nucleic acid with said first nucleic acid under hybridizing conditions; e) measuring a second elasticity of said first nucleic acid; and f) correlating the difference in said first elasticity and said second elasticity with the degree of hybridization.

In other embodiments the invention relates to a method of detecting the addition of a single nucleotide to a nucleic acid template comprising; a) providing: i) a single-stranded nucleic acid sequence wherein a portion of the said sequence is double-stranded, ii) a nucleotide, iii) a solid support, and iv) a force spectrometer; b) immobilizing said single-stranded nucleic acid sequences to said solid support; c) measuring the elasticity of said single-stranded nucleic acid sequence using said force spectrometer; d) mixing said single nucleotide phosphate with said single-stranded nucleic acid sequence under conditions such that said single nucleotide phosphate incorporates into said double-stranded portion within said single-stranded nucleic acid sequence; e) measuring the elastic response of said single-stranded DNA sequence with said single nucleotide phosphate incorporated into said double-stranded portion; and f) correlating the change in said elastic response with the incorporation of said nucleotide.

In some embodiments, the invention relates to a method comprising: a) providing i) a plurality of oligonucleotides containing 6 (six) or more contiguous nucleotides covering all possible sequences for a given number of nucleotides; ii) a substrate comprising a nucleic acid conjugate comprising a single-stranded portion complimentary to one of said plurality of oligonucleotide, a distance marker, and a molecular handle; wherein a first end of said single-strand is immobilized to the substrate and wherein a second end of said single-strand is linked to said distance marker and molecular handle; iii) an instrument configured to exert force on said molecular handle; b) mixing one of said oligonucleotide and said substrate under conditions such that said oligonucleotide hybridizes to said nucleic acid conjugate; c) moving said molecular handle with said instrument under conditions such that the nucleic acid is stretched; d) measuring a distance of said distance marker from said substrate; f) correlating said measured distance to a presence of said complimentary oligonucleotide sequence in said nucleic acid; and g) reconstructing the sequence of said nucleic acid conjugate of the substrate from the partial sequences of hybridized complementary nucleotides.

In additional embodiments, the invention relates to a substrate comprising; a single-stranded nucleic acid sequence comprising a first end and a second end wherein said single-stranded nucleic acid comprises an optical probe and a magnetic particle wherein said first end of said single-stranded nucleic acid is immobilized to the substrate and wherein said second end is linked to said optical probe and magnetic particle.

In some embodiments, the invention relates to chemical and enzymatic methods for attachment of nucleic acid fragments to the surface and to the near-field probes.

In other embodiments, the invention relates to microfluidic platforms for automated reagent delivery for single nucleotide addition cycling preferably using a force spectroscopy setup.

In other embodiments, the invention relates to probes used as markers and reporters of the distance from the surface of a solid support. The probes are selected from i) dielectric spheres, for instruments based on evanescent field scattering, ii) semiconductor quantum dots (QD), for instruments based on total internal reflectance fluorescence (TIRF), or iii) metal nanoparticles, for instruments based on capacitance changes.

In some embodiments, the invention relates to magnetic probes to exert force on single-stranded fragments anchored to a surface wherein these magnetic particles either simultaneously function as near-field probes or are used in tandem with near-field probes.

In additional embodiments, the invention relates to selective surface chemistry for attachment of DNA fragments to i) the surface of the solid support; ii) nanometer sized dielectric spheres, QD, and metal nanoparticles or composite probes thereof.

In some embodiments, the invention relates to methods of numerical modeling (e.g. 2D and 3D numerical solutions of Maxwell equations) evanescent field scattering and fluorescence of sub-wavelength (nanometer scale) particles and methods to use modeling to provide guidance in optimizing electromagnetic response of near-field probes in the vicinity of the surface.

In additional embodiments, the invention relates to methods of using sequencing technology platforms by combining force spectroscopy setup with microfluidic systems for efficient automated cycling of single nucleotide addition.

In some embodiments, the invention relates to methods of hybridization for distinct oligo tags, preferably with 8- to 20-mers, in a freely arrayed, preferably 100×100, matrix of single molecules by photometry of dielectric spheres or TIR fluorescence of QD preferably with random thermal forces only.

In additional embodiments, the invention relates to methods of generating a full force-extension profile, using force microscopy, and detecting, in a single synthetic DNA fragment elongation of a double-stranded nucleic acid by a single nucleotide by polymerase and combining force microscopy and near-field probes, to correlate measurements of end-to-end distances.

In some embodiments, the invention relates to methods of detecting changes in electromagnetic (photonic) response of near-field probes upon single nucleotide addition to an unknown nucleic acid sequence.

In additional embodiments, the invention relates to methods of reading unknown sequences of individual nucleic acid fragments in a, preferably 100×100 or larger, array using combined force spectroscopy and microfluidics setups.

In some embodiments, the invention relates to fabricating components of a massively parallel device using arrays of freely arrayed single molecules preferably with nucleotide incorporation rates preferably of up to 1 Mb/sec.

In some embodiments, the invention relates to methods of the simultaneous use of magnetic handles to exert force and quantum dots, or other distance markers, to read the molecular distance.

In additional embodiment, the invention relates to sequencing methods using magnifying tags for specific nucleotides.

In other embodiments, the invention relates to nanometer-sized near field probes for force spectroscopy of nucleic acid fragments attached to the surface of the solid substrate, preferably these probes: i) specifically bind to the nucleic acid fragments; ii) exert mechanical force on the nucleic acid; iii) provide reading of the end-to-end molecular extensions.

In other embodiments, the invention relates to elasticity measurements based on young's modulus.

A BRIEF DESCRIPTION OF THE FIGURES

Figure 6:
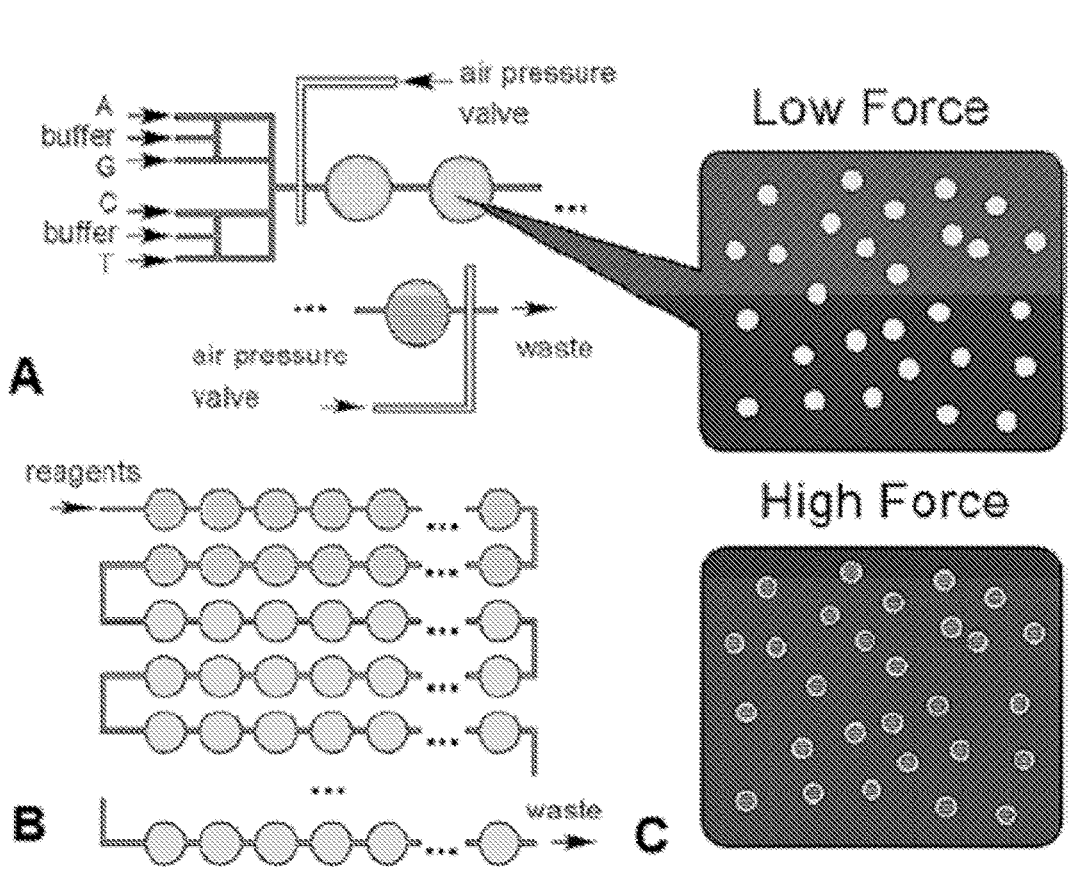

FIG. 6 illustrates a schematic diagram of microfluidic device for automated delivery of stock solutions of dNTPs and wash buffers (A). Individual reaction chambers suitable for FS on freely arrayed DNA fragments can be arranged as an array of chambers for parallel reactions of SNA (B). Freely arrayed single molecules display different brightness of the scattered (fluorescent) light depending on the distance from the surface FE curves are reconstructed from intensity profiles (C).

Figure 7:
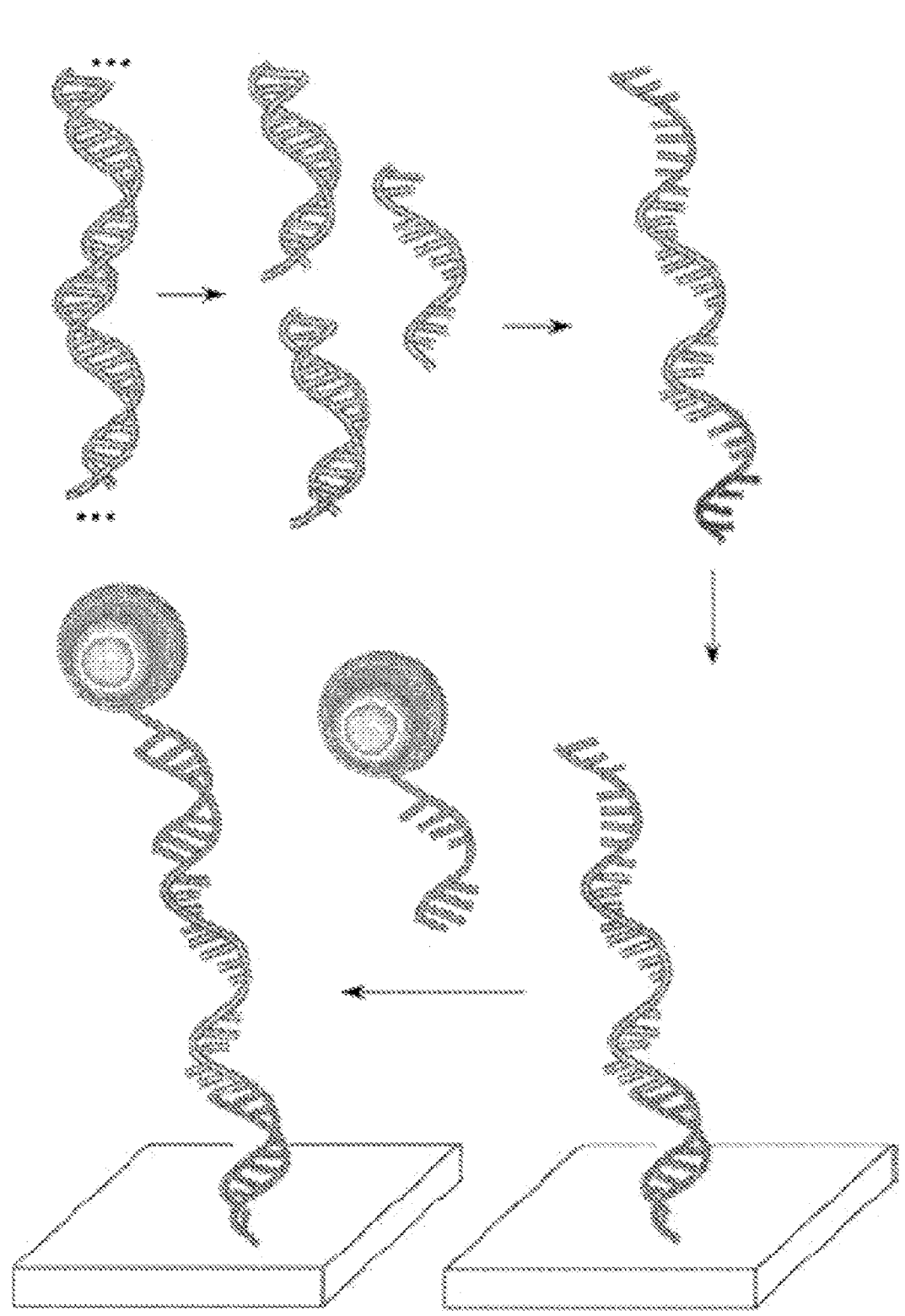

FIG. 7 shows a schematic diagram for surface modification of the microfluidic chip for force spectroscopy using near-field probes: DNA is first fragmented, then ligated with adaptors recognizing either surface or probe complimentary adaptors (or ligands), followed by hybridization (or binding) with recognition sites on the surfaces of the support and probe.

Figure 8:
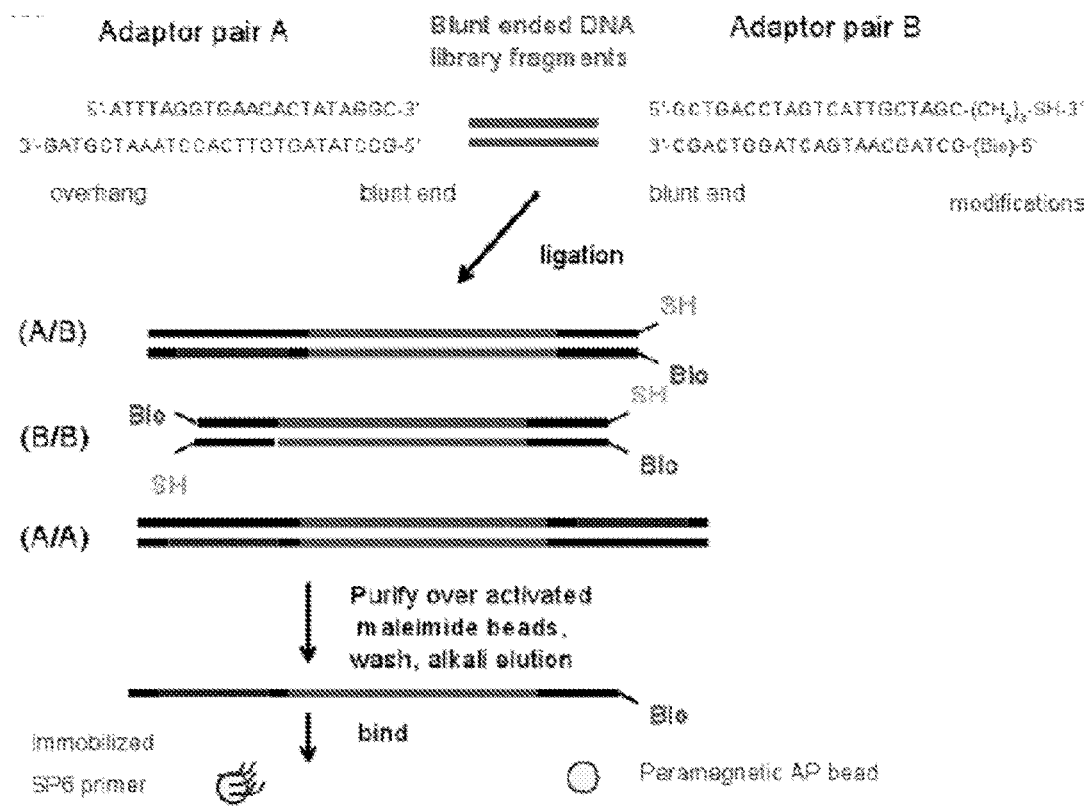

FIG. 8 shows DNA fragments for surface attachment.

Figure 9:
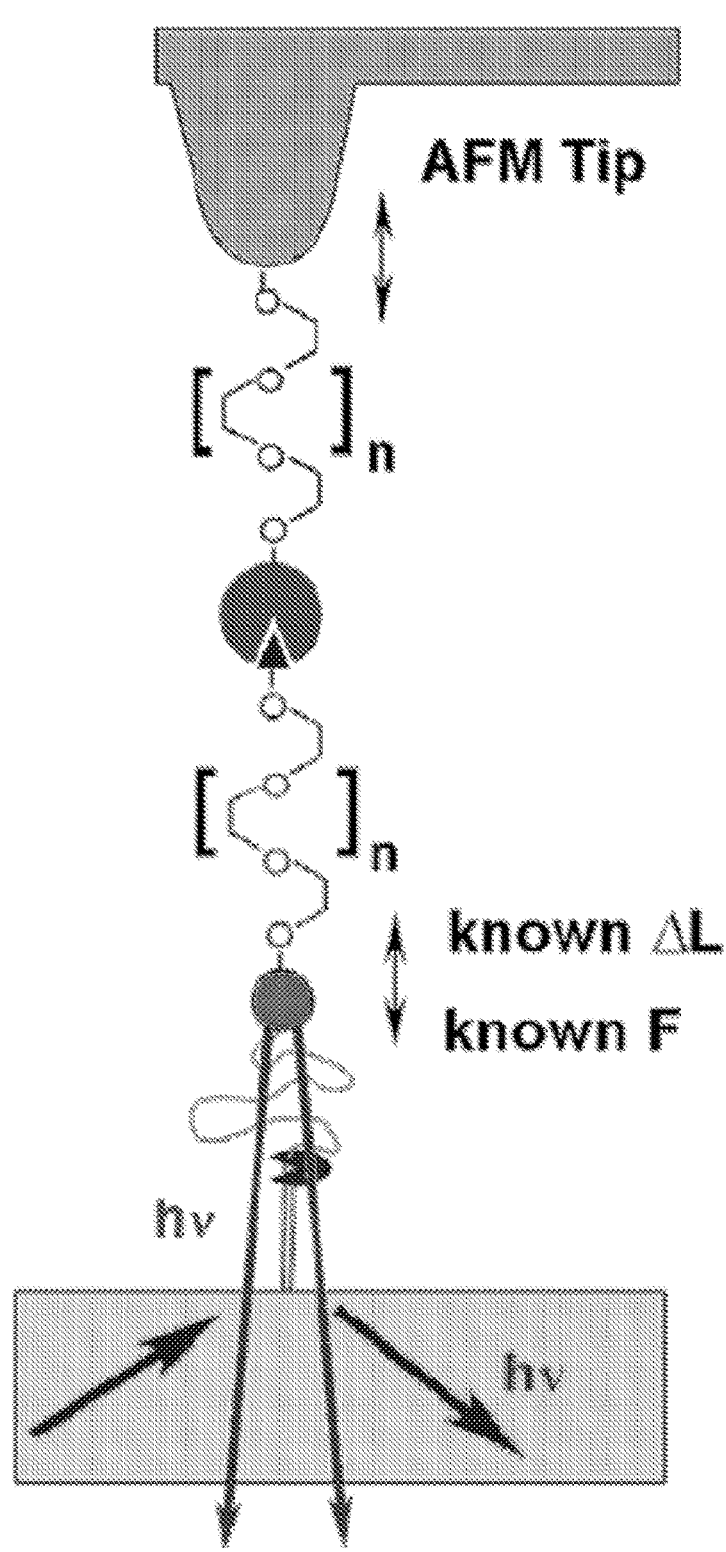

FIG. 9 illustrates a force spectroscopy experiment to test the response of the optical near-field probes to changes in the separation from the surface.

Figure 10:
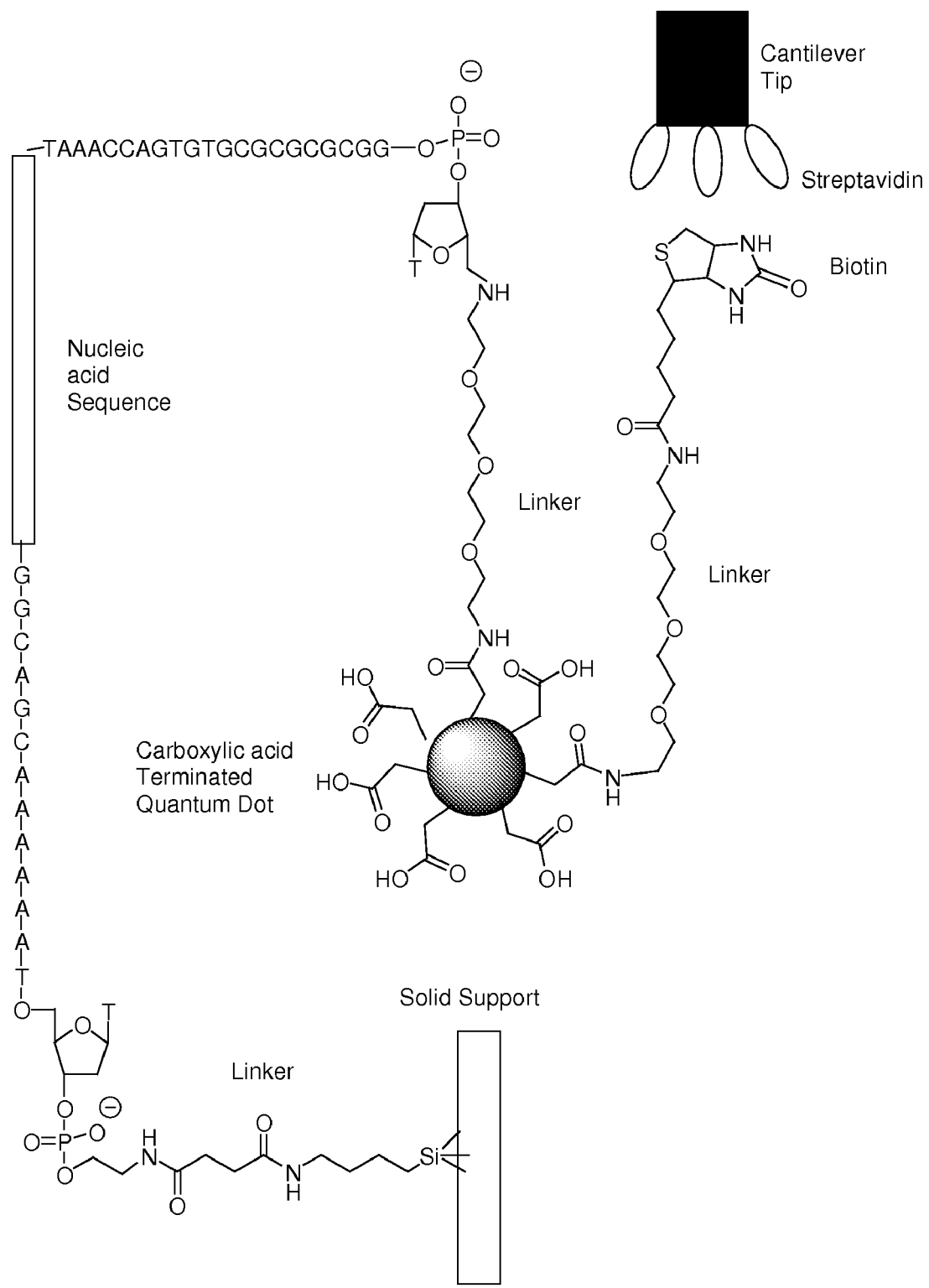

FIG. 10 (SEQ ID NOS:8-9) shows an embodiment that can be used in the force spectroscopy experiment illustrated in FIG. 9.

Figure 4:
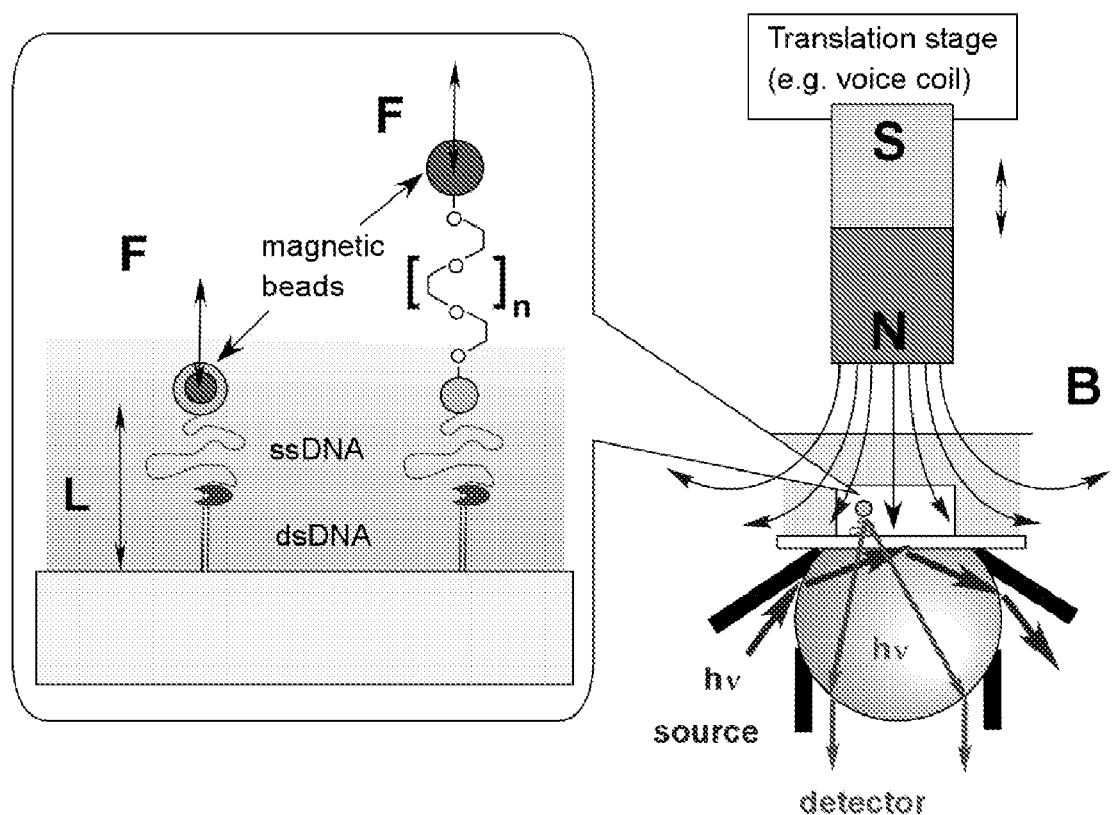
FIG. 4 illustrates embodiments of magnetic tweezers force spectroscopy assay with near-field probes for detection of molecular end-to-end distances.
Figure 11:
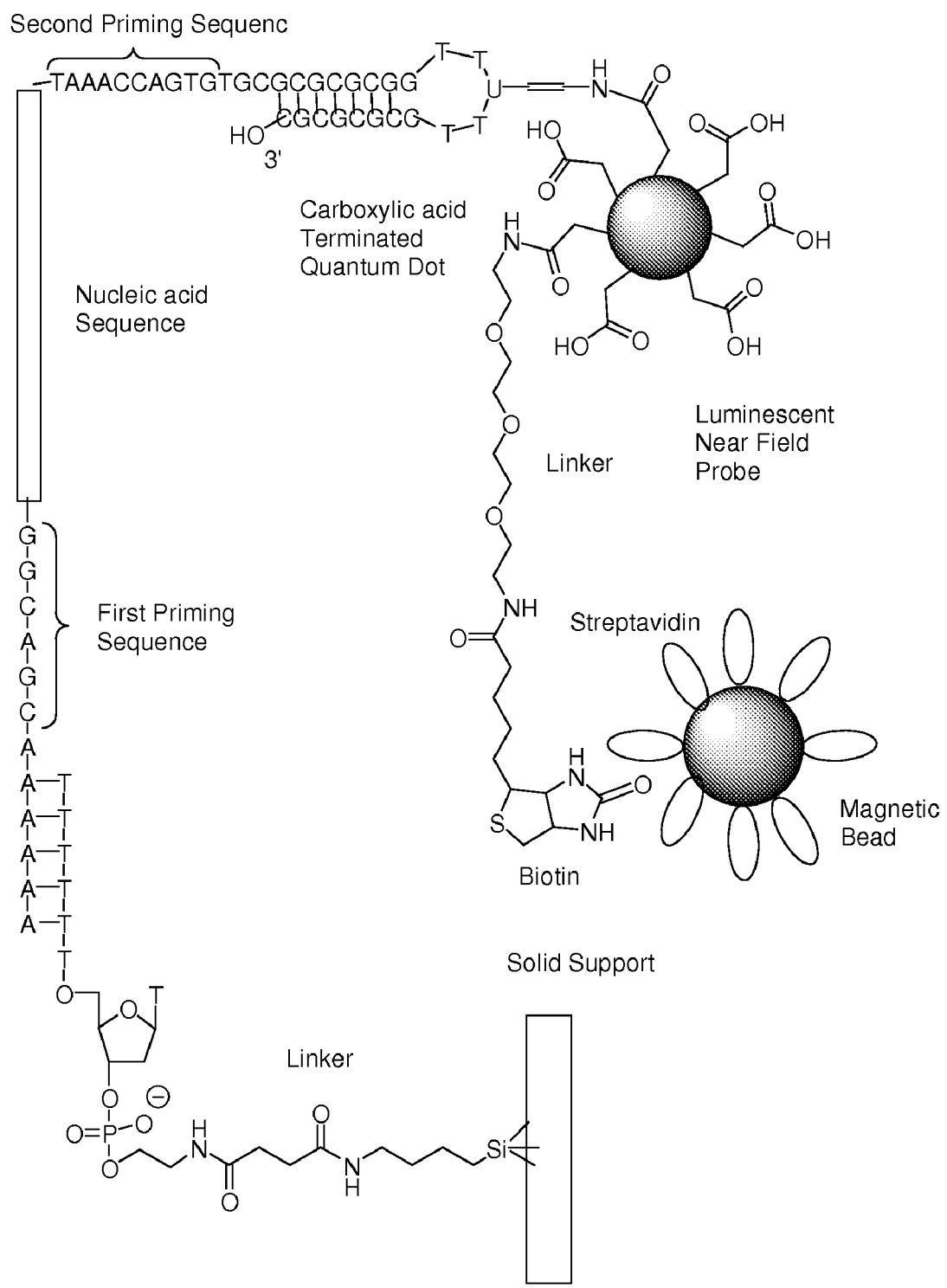

FIG. 11 shows an embodiment that can be used in the experiments illustrated in FIG. 4.

Figure 12:
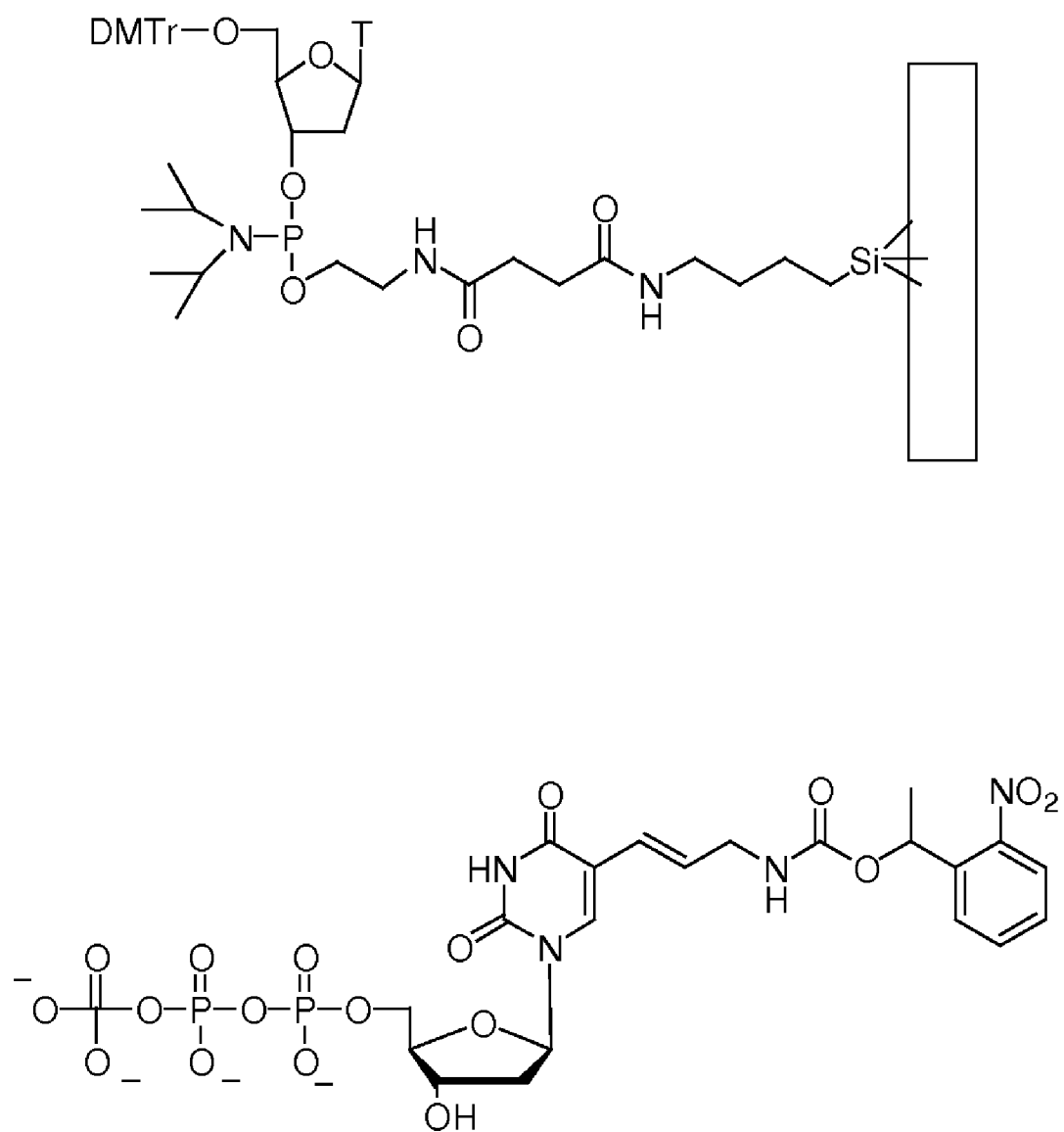

FIG. 12 shows intermediates that can be used to prepare the embodiment in FIG. 11 as describe in Seo et al. (2004) Proc. Natl. Acad. Sci. USA 101, 5488-5493, and Seliger et al. (1991) Nucleosides and Nucleotides 10, 303-306.

Figure 13:
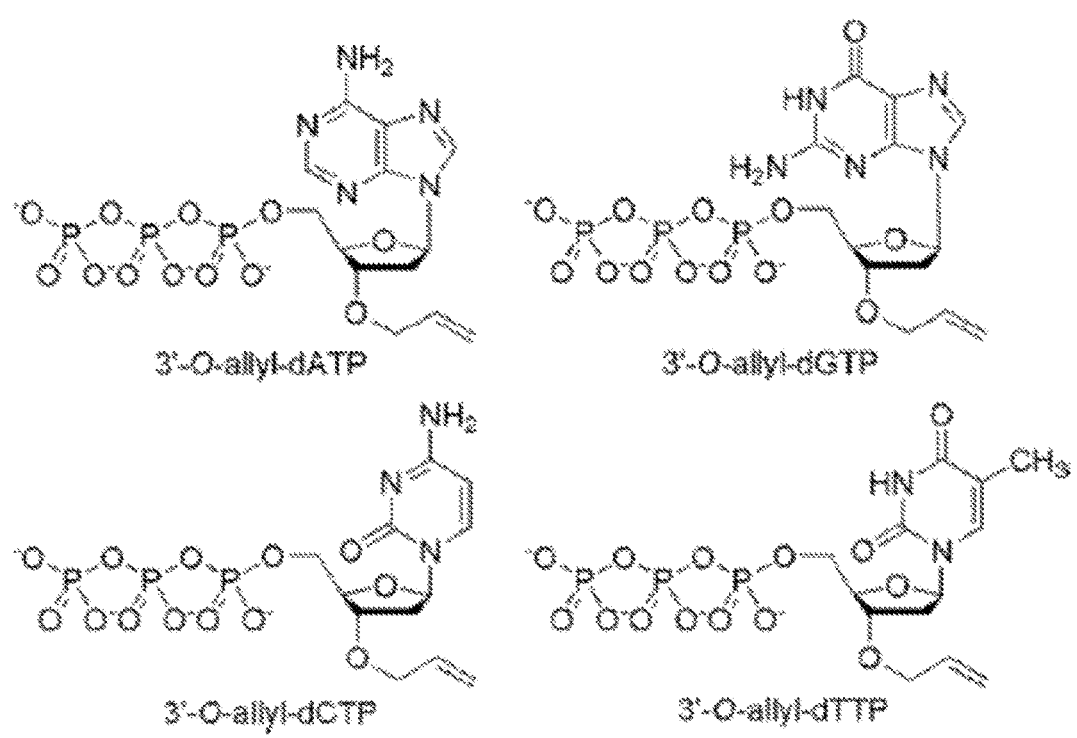

FIG. 13 shows nucleotides with 3' O-allyl protecting groups used as reversible terminators during sequencing methods as described in Ju et al. (2006) Proc. Natl. Acad. Sci. USA 103, 19635-19640.

Figure 14:
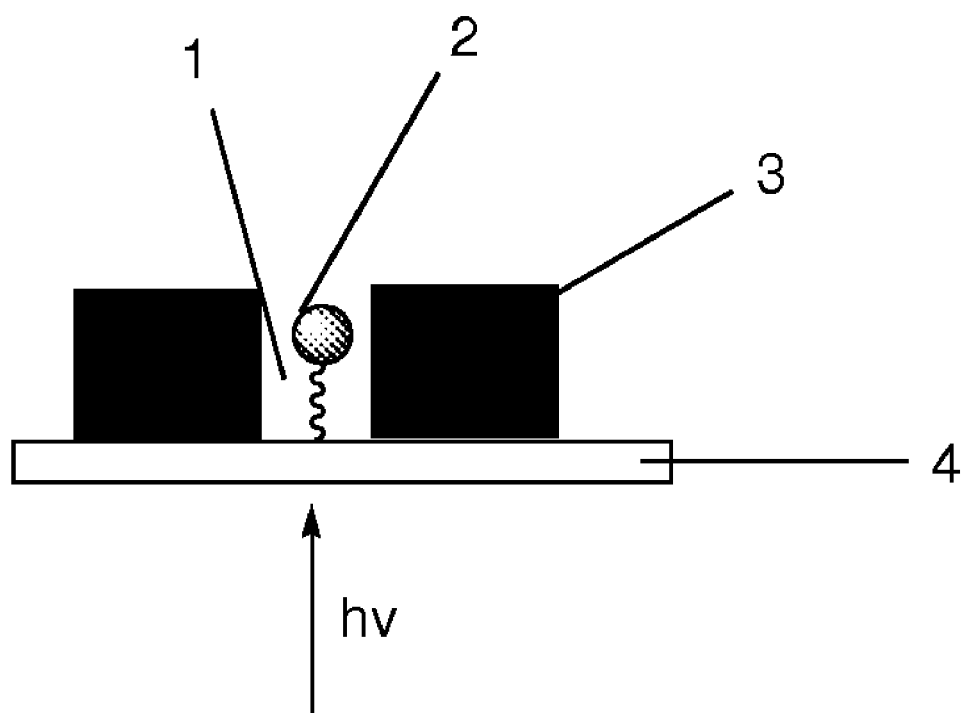

FIG. 14 illustrations one way of creating an evanescent field (1) by creating a zero-mode waveguide having an nucleic acid, molecular handle, and distance marker (2) immobilized to a transparent material (4). The transparent material is coated with an opaque film (3), preferably aluminum.

DETAILED DESCRIPTION OF THE INVENTION

The invention relates to stretch measurements of nucleic acids and correlating those measurements to the extent of double- and single-stranded content of a nucleic acid of interest, and to compositions and devices related thereto. In preferred embodiments, one performs the stretch or elasticity measurements under conditions such that one can determine a nucleic acid sequence or the presence of an oligonucleotide with a known sequence for the purpose of sequencing an unknown sequence in a sample.

TABLE 1

Key to the elements identified in the Figures.

Name of Element

FIG. 1

| | |
|---|---|
| 100 | substrate |
| 110 | single stranded DNA |
| 120 | double stranded DNA |
| 130 | DNA polymerase |
| 140 | bead |

FIG. 3

| | |
|---|---|
| 150 | objective lens for electron multiplying CCD camera |
| 160 | case |
| 170 | chamber |
| 180 | DNA with bead attached to substrate |
| 190 | bead |
| 200 | glass slide |
| 210 | optical near-field dove prism |
| 220 | hv emitted from illuminted bead (red) |
| 230 | hv emitted from light source (blue) |
| 240 | evanescent waves |
| 250 | total internal reflection fluorescence microscope (TIRFM) objective (grey sphere) |
| 260 | yellow wave guide |

FIG. 4

| | |
|---|---|
| 270 | small circle dNTP |
| 280 | fluorescet bead |
| 290 | magnetic bead |
| 300 | magnet S |
| 310 | magnet N |
| 320 | magnetic waves |
| 330 | source |
| 340 | detector |

FIG. 5

| | |
|---|---|
| 350 | inset graph avg = 0 for no SNA addition - red curve |
| 360 | inset graph avg ~0.19 nm for SNA - blue curve |
| 370 | red line - 110 bases |
| 380 | blue line - 111 bases |
| 390 | black line 100 bases |

FIG. 7

| | |
|---|---|
| 400 | double stranded DNA |
| 410 | restriction endonuclease |
| 420 | isolated excised single stranded fragment |
| 430 | ligase |
| 440 | single stranded DNA complementary to bead fragment |
| 450 | single stranded DNA complementary to primer |
| 460 | complementary primer fragment to 450 |
| 470 | complementary fragment for 440 attached to a bead |
| 480 | substrate |

FIG. 9

| | |
|---|---|
| 490 | Atomic Force Microscope Tip |
| 500 | n = number of dNTP |
| 510 | dNTP |
| 520 | biotin |
| 530 | Streptavidin |

In preferred embodiments, the invention is related to methods and systems based on concepts of mechanical properties of single molecules, according to which one may detect changes in molecular elasticity of a single nucleic acid fragment as one converts it from a single-stranded to double-stranded form. While applicant will not be bound by this or any other theory of the technique, one can use the technique to detect the addition of a single nucleotide to a nucleic acid molecule, catalyzed by DNA polymerase, preferably under conditions in which the polymerase activity is reduced or arrested. In preferred embodiments, the nucleic acid sequence is reconstructed from the order of addition of successively added deoxynucleoside triphosphates.

In another preferred embodiment of the invention, one uses single molecule force spectroscopy to detect changes in the conformation of the nucleic acid fragments attached to the surface of a solid support. Upon addition of a single nucleotide, the fraction of base pairs (bp) in a double-stranded (ds) nucleic acid segment increases, while the corresponding single-stranded (ss) nucleic acid fragment undergoes a complementary decrease in the number of bases. One detects changes imparted to the mechanical properties and dynamics of the nucleic acid segment upon conversion from ss to ds forms. It is contemplated that one can acquire stretch measurements by force spectroscopy in various formats (scanning probe, magnetic or optical tweezers). Detecting a change in elasticity of the nucleic acid is equivalent to detecting the addition of a nucleotide, thus providing (if the identity of the added nucleotide is known) the means of reading the unknown nucleic acid sequence after successive additions are made. Runs of the same nucleotides, e.g., AA, AAA, may be detected using nucleotides with reverse terminators implied through the magnitude of the response when exposed to a solution that is limited to one specific nucleotide.

In other embodiments, it is contemplated that one may create stock solutions of oligonucleotides with known sequences that cover all possible sequences. For example, one may create 32 stock solutions of 4-mers. If each stock solution contains only one particular oligonucleotide sequence then the summation of stock solutions contain every possible combination of an oligonucleotide with 4 nucleotides. Similarly, one may create 65,000 stock solutions of 8-mers. Thus applying the methods disclosed herein, one may use these stock solutions to determine a particular sequence when ligation or hybridization is occurs.

Force spectroscopy of single biomolecules is a tool for unraveling mechanics of single biomolecules and polymers. A typical experiment involves i) grabbing (e.g. by a biotin-avidin link) a free end of the biomolecule or polymer that is attached at its other end to a solid support, and ii) pulling by the grabbed end, while recording the pulling force, to generate a force-extension (FE) curve. While applicants will not be bound by any theoretical explanation of any applications of the invention, statistical mechanical models of polymer chains may describe the mechanical response of the system.

The model description of the system has improved to the level that it is possible to fit force-extension curves to determine molecular end-to-end distances with sub-nanometer precision. This analysis applies to experiments on both synthetic polymers in good solvents and biological heteropolymers such as proteins and nucleic acids. The ability to determine the end-to-end distance to an accuracy of a single chemical bond (~0.1 nm) provides a "molecular ruler" with which to study changes in molecular conformation. For example, the change in contour length when a region of green fluorescent protein is unfolded, as determined from experimental FE curves, was used to assign conformational changes in the protein with resolution at the level of a single amino acid residue.

Figure 1:
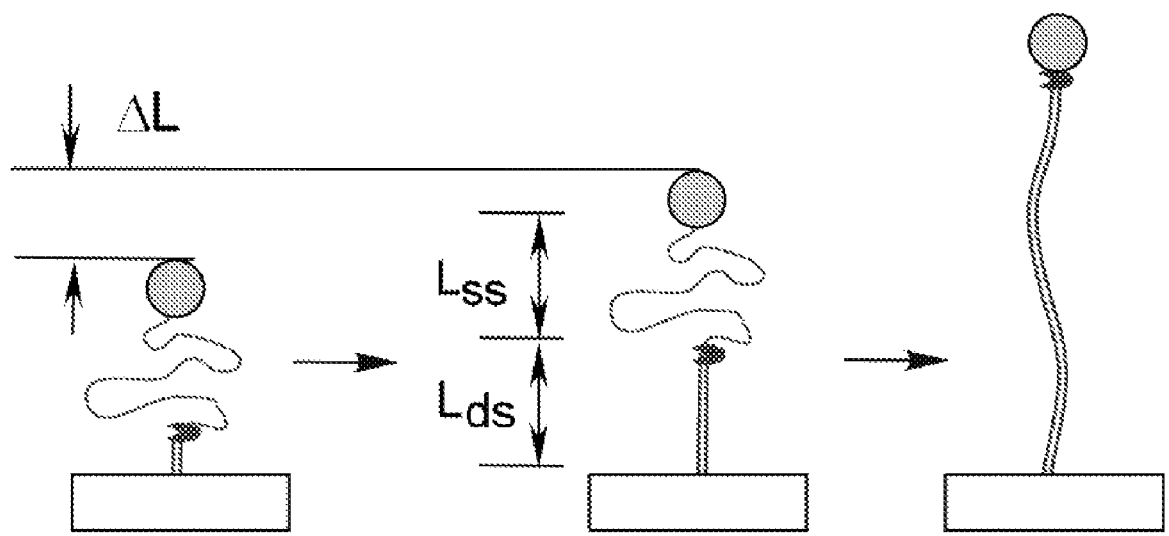
FIG. 1 illustrates a change in the conformation of the surface-bound nucleic acid fragment in the course of replication of a single-stranded nucleic acid by DNA polymerase.

The behavior of nucleic acids in both single- and double-stranded forms can be described by a set of statistical models for polymer chains: from extensible free-jointed chain (FJC) to extensible worm-like chain (WLC) models (see FIG. 1). According to this description, when the chains (i.e. DNA backbone) are stretched by the application of an external force, the length of a single monomer unit (per base pair) can increase due to changes in the bond angles and (to a lesser extent) bond lengths as they adjust to accommodate the stress.

Thus, the conventional models of statistical mechanics of polymer chains account for bond elasticity if one treats the chain as "extensible." More importantly, the mechanical behavior of the polymer chain, by this description, is primarily determined by the entropic elasticity, which is highly responsive to the change in persistence length (lp) of the polymer (the distance over which the correlations in the polymer chain are lost—looking at the molecule on scales shorter than lp, the molecule appears straight; looking from a distance>>lp, the molecule will appear randomly coiled).

According to the model, the change experienced by the DNA molecule is the change in its stiffness: in the ss-DNA, the are free to orient in solution in any possible way, while in the dsDNA, the bp must remain hydrogen bonded in Watson-Crick pairing and maintain this orientation even under external force. This structural difference is responsible for two orders of magnitude difference in persistence length for the two forms of DNA -0.75 nm (~3 bp) for ssDNA versus 50 nm (~150 bp) for dsDNA. Change in the stiffness of the nucleic acid upon conversion from single-stranded to double-stranded form, as manifested by the different lp, is many embodiments of the invention.

Surface Immobilization of Nucleic Acid Linked to Molecular Handles and Distance Markers In some embodiments, the invention exploits surface chemistry to attach nucleic acid fragments to flat surfaces in a well-defined orientation. One may use high-resolution microscopy to observe freely arrayed nucleic acid fragments on the surface of glass. For the detection of the distance between the free end and the surface, one may set up optical evanescent fields in the vicinity of the glass-aqueous solution interface. Such evanescent fields (or optical near-fields) in certain embodiments, may be generated using a total internal reflection (TIR) configuration for the illumination of the glass-solution interface on slab waveguides or zero-mode waveguides. In a TIR arrangement, radiation from an optically dense medium is incident onto an optically less dense medium at angles larger than the critical angle, i.e. the angle at which all incident energy is reflected back into an optically dense medium. In spite of the fact that no radiation propagates in the medium (the solution containing DNA fragments), the electromagnetic fields penetrate into the second medium a short distance from the interface.

In some embodiments, in order to observe the distance between the free end and the surface of the support, one attaches optical probes to these free ends. These optical probes interact with the near-field and generate some propagating fields whose amplitude depends on the intensity of the evanescent field, therefore, directly reporting the position of the probe within the evanescent field (see FIG. 5).

For fluorescent probes one can use semiconductor nanocrystals, such as quantum dots (QDs). Quantum dots have sizes that are in the range where quantum confinement effects become important, energy gap becomes size-dependent and, thus, the fluorescence wavelength for the same semiconductor shifts with changes in the diameter of the QD. The QDs also have a large absorbance cross-section over a broad frequency range, and therefore, fluorescence of QDs of different sizes can be excited by the same light source. The small size (<<length of the DNA fragment) and high quantum efficiency of QDs and reduced photobleaching make them preferable as probes of the optical near-field.

The function of these optical near-field probes is to provide photonic response (scattering or fluorescence) whose intensity is directly related to intensity of the near-field (which, in turn, is a function of the separation from the surface). While embodiments of the invention will typically use optical response as the detection method, the approach is different from the use of fluorescent dNTPs: i) Due to the size of the probes preferred, the optical signal is orders of magnitude higher, thus, eliminating the need for high concentration of DNA or secondary amplification steps, and enabling an assay to be carried out in a single molecule format; ii) QD optical probes do not bleach, thus continuous monitoring and prolonged use of high intensity sources (lasers) is possible; iii) The probes report on the parameter describing the whole molecule (end-to-end distance) rather than the specific base added, thus no separation step is needed for base calling in a given step, and the whole assay will be accelerated accordingly.

In preferred embodiments of the invention, probes are used as markers and reporters of the distance from a substrate. As used herein, a "distance marker" means any molecular arrangement that is configured to indicate the distance or relative distance of the arrangement in relation to the substrate on which the marker is immobilized. In more preferred embodiments, the distance markers are near-field probes selected from i) dielectric spheres, for detection with instruments based on evanescent field scattering, ii) semiconductor quantum dots (QDs), for detection with instruments based on total internal reflectance fluorescence (TIRF), or iii) metal nanoparticles, for detection with instruments based on capacitance changes.

For dielectric probes, one can use polystyrene spheres, because i) they are available commercially in a variety of sizes (from 20 nm to microns); ii) their surface chemistry has been well-characterized and numerous surface modifications have been reported; iii) they provide an excellent refractive index contrast (index of 1.59 versus 1.33 of water), and iv) they can be doped with magnetic particles. If a higher refractive index contrast is desired one can use titania dioxide (n~2.4-2.7) nanoparticles (or commercially available submicron particles from DuPont). The chemistry of titania dioxide surfaces is also readily modified using, for example, siloxane-based surface attachment of reactive organic functional groups.

As used herein, a "molecular handle" means any molecular arrangement that is configured to move upon the action of a force. In preferred embodiments, molecular handles are magnetic particles that move under the force of a magnet, and polystyrene particles that move under the force of light. In other preferred embodiments, the molecular handles and distance markers (near-field probes, e.g. semiconducting nanoparticles) are attached to the single stranded nucleic acid fragments. It is specifically contemplated that the molecular handle and distance marker are a part of the same molecular arrangement or particle or composite particles such as CdTe doped sodium silicate particles. As handles, they are used to actuate the single molecule in an array of single molecules; while as distance markers, they report marker locations. The synthesis of composite particles such as 1) CdTe nanocrystals capped with 1-mercapto-2,3-propandiol, 2) CdSe nanocrystals capped with sodium citrate, and 3) core-shell CdSe/CdS nanocrystals capped with sodium citrate is described in Rogach et al., Chem. Mater. 2000, 12, 2676-2685. One may modify these surfaces with 3-mercaptopropyltrimethoxysilane (MPS) in water-ethanol mixtures. By addition of sodium silicate, "raisin bun"-type composite particles form, with either CdTe, CdSe, or CdSe/CdS nanocrystals which are homogeneously incorporated as multiple cores into silica spheres of 40-80 nm size. Further, growth of larger silica spheres (100-700 nm) can be performed by using either MPS-modified semiconductor nanocrystals or "raisin bun"-type composite particles as seeds, which gives semiconductor-doped silica globules of desirable sizes in the submicrometer range. One observes a shift of the photonic band gap to the red in photonic crystals made of nanoparticles-doped silica due to the refractive index of the semiconductors.

A laser beam brought to a focus with a strongly converging lens forms a type of optical trap widely known as an optical tweezer. Multiple beams of light passing simultaneously through the lens' input pupil may focus to multiple optical tweezers, each at a location determined by the associated beam's angle of incidence and degree of collimation as it enters the lens. Their intersection at the input pupil yields an interference pattern whose amplitude and phase corrugations characterize the downstream trapping pattern. Imposing the same modulations on a single incident beam at the input pupil would yield the same pattern of traps. Such wavefront modification can be performed by a computer-designed diffractive optical element (DOE), or hologram. Holographic optical trapping (HOT) uses computer-generated holograms (CGHs) to project arbitrary configurations of optical traps, and so provides control over microscopic materials dispersed in fluid media. In some embodiments, one uses optical traps to move particles linked to nucleic acids, including quantum dots.

Quantum dots are semiconductor particles preferably with diameters of the order of 2-10 nanometers, or roughly 200-10,000 atoms. As a semiconductor material, quantum dots have a composition-dependent bandgap energy, which is the minimum energy required to excite an electron to an energy level above its ground state, commonly through the absorption of a photon of energy greater than the bandgap energy. Relaxation of the excited electron back to its ground state results in photon emission. Because the bandgap energy is dependent on the particle size, the optical characteristics of a quantum dot can be tuned by adjusting its size. A synthetic method for quantum dots (<5% root-mean-square in diameter) made from cadmium sulfide (CdS), cadmium selenide (CdSe), or cadmium telluride (CdTe) is described in Murray et al. (1993) J. Am. Chem. Soc. 115, 8706-8715. Quantum dots that can span the visible spectrum are known, and CdSe has become the preferred chemical composition for quantum dot synthesis. Many techniques are possible for post-synthetically modified quantum dots, such as coating with a protective inorganic shell (Dabbousi et al. (1997) J. Phys. Chem. B 101, 9463 -9475, and Hines et al. (1996) J. Phys. Chem. 100, 468-471); surface modification (Gerion et al. (2001) J. Phys. Chem. B 105, 8861-8871, and Gao et al. (2003) J. Am. Chem. Soc. 125, 3901-3909) and direct linkage to active molecules (Bruchez et al. (1998) Science 281, 2013-2016, and Chan et al. (1998) Science 281, 2016-2018). CdSe quantum dots with diameters between 2 and 8 nm have emission wavelengths from 450-650 nm, spanning the entire visible spectrum. By also adjusting the quantum dot composition (ZnS, CdS, CdSe, CdTe, PbS, PbSe, and their alloys), it is possible to span the wavelength range 400-4000 nm.

Because quantum dots have high surface area to volume ratios, a large fraction of the constituent atoms are exposed to the surface, and therefore have atomic or molecular orbitals that are not completely bonded. These "dangling" orbitals may form bonds with organic ligands such as trioctylphosphine oxide (TOPO). Strategies may be used to make hydrophobic quantum dots soluble in aqueous solution. In one instance, a suspension of TOPO-coated quantum dots is mixed with a solution containing an excess of a heterobifunctional ligand, which has one functional group that binds to the quantum dot surface and another functional group that is hydrophilic. Thereby, hydrophobic TOPO ligands are displaced from the quantum dot through mass action, as the new bifunctional ligand adsorbs to render water solubility. Using this method, (CdSe)ZnS quantum dots may be coated with mercaptoacetic acid and (3-mercaptopropyl) trimethoxysilane, both of which contain basic thiol groups to bind to the quantum dot surface atoms, yielding quantum dots displaying carboxylic acids or silane monomers. Quantum dots covered with carboxylic acid groups may interact directly with molecules containing basic functional groups, such as amines or thiols. Thus, nucleotides and nucleic acids functionalized with amine or thiol groups, as disclosed herein, can be linked to quantum dots.

The term "conjugate", as used herein, refers to any compound that has been formed by the joining of two or more moieties. A "moiety" is any type of molecular arrangement designated by formula, e.g., chemical name or structure. Within the context of certain embodiments, a conjugate is said to comprise one or more moieties. This means that the formula of the moiety is substituted at some place in order to be joined and be a part of the molecular arrangement of the conjugate. In a preferred embodiment, we refer to nucleic acid conjugates meaning that the nucleic acid is one moiety. It is not intended that the joining of two or more moieties must be directly to each other. A linking group, i.e., any molecular arrangement that will connect the moieties by covalent bonds such as, but not limited to, one or more amide group(s). Alkyl groups and ethylene glycol units, may join the moieties, i.e., covalent linking. Additionally, although the conjugate may be unsubstituted, the conjugate may have a variety of additional substituents connected to the linking groups and/or connected to the moieties.

As used herein, the term "immobilization" refers to the attachment or entrapment, either chemically or otherwise, of a material to another entity (e.g., a solid support) in a manner that restricts the movement of the material. For example, a nucleic acid may be immobilized to a solid support by hybridizing to a complimentary sequence or by directly linking the molecule to the support through covalent bonds.

As used herein, the term "ligand" refers to any molecule that binds to or can be bound by another molecule. Examples of ligands include, but are not limited to, molecules such as biotin, carbohydrates, peptide, antigens, nucleic acids and other substance that binds to another entity to form a complex.

A "receptor" means a moiety utilized to selectively bind to a ligand.

As used herein, the term "selective binding" refers to the binding of one material to another in a manner dependent upon the presence of a particular molecular structure (i.e., specific binding). For example, an immunoglobulin will selectively bind an antigen that contains the chemical structures complementary to the ligand binding site(s) of the immunoglobulin. This is in contrast to "non-selective binding," whereby interactions are arbitrary and not based on structural compatibilities of the molecules.

As used herein, the term "substrate" refers to a solid object or surface upon which another material is layered or attached such as mesogens. Solid supports include, but are not limited to, glass, metals, gels, and filter paper, among others.

As used herein, the term "sample" is used in its broadest sense. In one sense it can refer to a biopolymeric material. In another sense, it is meant to include a specimen or culture obtained from any source, as well as biological and environmental samples. Biological samples may be obtained from animals (including humans) and encompass fluids, solids, tissues, and gases. Biological samples include blood products, such as plasma, serum and the like. Environmental samples include environmental material such as surface matter, soil, water, crystals and industrial samples. These examples are not to be construed as limiting the sample types applicable to the present invention.

Sequencing-by-synthesis is based on the detection of nucleotide incorporation, using a primer-directed polymerase extension. The sequence can be deduced iteratively. Various protocols are based on fluorescently labeled nucleotides. In some embodiments, the present invention relates to methods of sequencing by synthesis that utilize unlabeled or unmodified nucleotides by detecting stretching properties of nucleic acids with a proximity probe.

A proximity probe microscope works by measuring a local property—such as height, optical absorption, or magnetism—with a probe or "tip" placed close to the substrate. The small probe-substrate separation makes it possible to take measurements over a small area. One may acquire an image when the microscope raster-scans the probe over the substrate while measuring the local property in question. One can use a variety of tip types. The "normal tip" is a 3 μm tall pyramid with ~30 nm end radius. In some preferred embodiments, one uses tips with higher aspect ratio (i.e., long and thin) such as electron-beam-deposited (EBD) tips or those made by microlithography processes. In other preferred embodiments, the tips are coated with a film of gold so that thiol based linking groups can be attached directly to the tip, or the entire probe.

An atomic force microscope, "AFM", operates by measuring attractive or repulsive forces between a tip and the sample. In its repulsive "contact" mode, the instrument lightly touches a tip at the end of a leaf spring or "cantilever" to the sample. A detection apparatus measures the vertical deflection of the cantilever. Thus, in contact mode the AFM can measure repulsion forces between the tip and sample. AFMs can image samples in air and under liquids.

AFMs can generally measure the vertical deflection of the cantilever with high resolution. To achieve this, one may use an optical lever. The optical lever operates by reflecting a laser beam off the cantilever. Angular deflection of the cantilever causes several-fold larger angular deflection of the laser beam. The reflected laser beam strikes a position-sensitive photodetector consisting of photodiodes. The difference between the photodiode signals indicates the position of the laser spot on the detector and thus the angular deflection of the cantilever. AFM cantilevers have high flexibility. A high flexibility stylus exerts lower downward forces on the sample, resulting in less distortion.

Tube or stack piezoceramics position the tip or sample. Piezoelectric ceramics are a class of materials that expand or contract when in the presence of a voltage gradient or, conversely, create a voltage gradient when forced to expand or contract. One uses piezoceramics to create three-dimensional positioning devices of desired high precision. One can, preferably, use tube-shaped piezoceramics because they combine a simple one-piece construction with high stability and large scan range. For example, one can cover four electrodes on the outer surface of the tube, while a single electrode covers the inner surface. Application of voltages to one or more of the electrodes causes the tube to bend or stretch, moving the sample in three dimensions.

AFMs can take measurements in a variety of ways, such as, but not limited to, recording the feedback output or the cantilever deflection. For example, an optical lever AFM can measure the friction between tip and sample. If the scanner moves the sample horizontal or perpendicular to the long axis of the cantilever, friction between the tip and sample causes the cantilever to twist. A position-sensitive photodetector can distinguish the resulting left-and-right motion of the reflected laser beam from the up-and-down motion caused by topographic variations. AFMs can image sample elasticity by pressing or pulling the tip into or out of the sample and measuring the resulting cantilever deflection. AFMs can also image the softness of a sample by pressing the cantilever into it at each point in a scan. The scanner raises the sample or lowers the cantilever by a preset amount, the "modulation amplitude". In response, the cantilever deflects an amount dependent on the softness of the sample: the harder the sample, the more the cantilever deflects.

As used herein, the term "ligate" in relation to nucleic acids and nucleotides means the process of joining two or more nucleic acids, nucleotides or combinations thereof by creating a covalent phosphodiester bond between the 3' hydroxyl of one nucleotide and the 5' phosphate of another. It is not intended to be limited to the actions of a DNA ligase, but also includes the actions of a DNA polymerase.

As used herein, the term "solid support" is used in reference to any solid or stationary material to which reagents such as antibodies, antigens, and other test components are attached. For example, the wells of microtiter plates provide solid supports. Other examples of solid supports include microscope slides, coverslips, beads, particles, cell culture flasks, as well as any other suitable item.

As used herein, a "bead" means a material with a periphery of preferably less that 1 millimeter and even more preferably less than one micrometer and greater than 100 nanometers in diameter. Preferably the bead is substantially spherical. The bead could also be shaped in a rod or cube, but it is not intended that the bead be limited to these shapes. Preferably the bead is made of a material that is stable to dissolution in the liquid in which it is to be suspended. Preferably the bead is made of a polymer or metal or a combination thereof, but it is not intended that the bead be limited to these materials. It is contemplated that the exterior surface of the bead may vary chemically from its internal chemical constitution.

As used herein, a "nucleotide" is a chemical compound that consists of a heterocyclic base, a sugar, and one or more phosphate groups. Preferably, the base nucleotide is a derivative of purine or pyrimidine, and the sugar is the pentose (five-carbon sugar) deoxyribose or ribose. Nucleotides are the monomers of nucleic acids, with three or more nucleotides covalently bonded together forming a "nucleotide sequence." As used herein, the term "nucleotide" is intended to include substituted nucleotides including conjugates linked to fluorescent moieties and those with protecting groups such as those illustrated in FIG. 13.

Nucleic acids are said to have a "5'-terminus" (5' end) and a "3'-terminus" (3' end) because nucleic acid phosphodiester linkages occur at the 5' carbon and 3' carbon of the pentose ring of the substituent mononucleotides. The end of a polynucleotide at which a new linkage would be to a 5' carbon is its 5' terminal nucleotide. The end of a polynucleotide at which a new linkage would be to a 3' carbon is its 3' terminal nucleotide. A terminal nucleotide, as used herein, is the nucleotide at the end position of the 3'- or 5'-terminus. A nucleic acid may be double-stranded or single-stranded.

Hybridization means the coming together (annealing) of a single-stranded nucleic acid with either another single-stranded nucleic acid or a nucleotide by hydrogen bonding of complementary base(s). Hybridization and the strength of hybridization (i.e., the strength of the association between nucleic acid strands) is impacted by many factors well known in the art including the degree of complementarity of the respective nucleotide sequences, stringency of the conditions such as the concentration of salts, the $T_m$ (melting temperature) of the formed hybrid, the presence of other components (e.g., the presence or absence of polyethylene glycol), the molarity of the hybridizing strands and the G:C content of the nucleic acid strands.

As used herein, the term "primer" refers to an oligonucleotide, whether occurring naturally (e.g., as in a purified restriction digest) or produced synthetically, capable of acting as a point of initiation of nucleic acid synthesis when placed under conditions in which synthesis of a primer extension product complementary to a nucleic acid strand is induced (i.e., in the presence of nucleotides, an inducing agent such as DNA polymerase, and under suitable conditions of temperature and pH). The primer is preferably single-stranded for maximum efficiency in amplification, but may alternatively be double-stranded. If double-stranded, the primer is first treated to separate its strands before being used to prepare extension products. In preferred embodiments, the primer is attached to the end of a nucleic acid such that a hairpin forms from self-hybridization. Preferably, the primer is an oligodeoxyribonucleotide. The primer must be sufficiently long to prime the synthesis of extension products in the presence of the inducing agent. The exact lengths of the primers will depend on many factors, including temperature, source of primer and use of the method. It is also contemplated that primers can be used in PCR (see below) to artificially insert desired nucleotide sequences at the ends of nucleic acid sequences.

As used herein, the terms "complementary" or "complementarity" are used in reference to a sequence of nucleotides related by the base-pairing rules. For example, the sequence 5' "A-G-T" 3', is complementary to the sequence 3' "T-C-A" 5'. Complementarity may be "partial," in which only some of the nucleic acids' bases are matched according to the base pairing rules. Or, there may be "complete" or "total" complementarity between the nucleic acids. The degree of complementarity between nucleic acid strands has significant effects on the efficiency and strength of hybridization between nucleic acid strands. This is of particular importance in amplification reactions, as well as for detection methods that depend upon hybridization of nucleic acids.

As used herein, the term "polymerase chain reaction" ("PCR") refers to the method described in U.S. Pat. Nos. 4,683,195, 4,889,818, and 4,683,202, all of which are hereby incorporated by reference. These patents describe methods for increasing the concentration of a segment of a target sequence in a mixture of genomic DNA without cloning or purification. This process for amplifying the target sequence consists of introducing a large excess of two oligonucleotide primers to the DNA mixture containing the desired target sequence, followed by a precise sequence of thermal cycling in the presence of a DNA polymerase (e.g., Taq). The two primers are complementary to their respective strands of the double stranded target sequence. To effect amplification, the mixture is denatured and the primers then annealed to their complementary sequences within the target molecule. Following annealing, the primers are extended with a polymerase so as to form a new pair of complementary strands. The steps of denaturation, primer annealing and polymerase extension can be repeated many times (i.e., denaturation, annealing and extension constitute one "cycle"; there can be numerous "cycles") to obtain a high concentration of an amplified segment of the desired target sequence. The length of the amplified segment of the desired target sequence is a controllable parameter, determined by the relative positions of the primers with respect to each other. By virtue of the repeating aspect of the process, the method is referred to as the "polymerase chain reaction" (hereinafter "PCR"). Because the desired amplified segments of the target sequence become the predominant sequences (in terms of concentration) in the mixture, they are said to be "PCR amplified."

With PCR, it is possible to amplify a single copy of a specific target sequence in genomic DNA to a level detectable by several different methodologies (i.e., hybridization with a labeled probe; incorporation of biotinylated primers followed by avidin-enzyme conjugate detection; incorporation of $^{32}$P-labeled deoxynucleotide triphosphates, such as dCTP or dATP, into the amplified segment). In addition to genomic DNA, any oligonucleotide sequence can be amplified with the appropriate set of primer molecules. In particular, the amplified segments created by the PCR process itself are themselves efficient templates for subsequent PCR amplifications.

A "marker" is a compound or composition detectable from background by its properties, including without limitation spectroscopic, photochemical, biochemical, immunochemical, and chemical. For example, useful markers include luminescent dyes, quantum dots, fluorescent proteins such as green, yellow, red or blue fluorescent proteins, radioactive elements, compounds enriched in particular atom isotopes, electron-dense reagents, enzymes (e.g., as commonly used in an ELISA), biotin, digoxigenin, or haptens and proteins for which antisera or monoclonal antibodies are available.

Luminescence is a property of certain materials that renders them capable of absorbing electromagnetic energy of a given wavelength and emitting at a different wavelength. Examples include fluorescence, bioluminescence and phosphorescence. Luminescence can be caused by chemical or biochemical changes, electrical energy, subatomic motions, reactions in crystals, or other, generally non-thermal, stimulation of the electronic state of an atomic system.

A "luminescent marker" is a molecular construction capable of emitting light, that is bound, either covalently, generally through a linker, or through ionic, van der Waals, hydrogen bonds, or any physical spatial constraint to another material, substance, or molecule. Preferably a luminescent marker is a molecule with aromaticity or a molecule with highly conjugated double bonds as typically found in fluorescent dyes, or quantum dots or combinations thereof. In preferred embodiments, dyes are linked to a nucleotide by the formation of amide bonds that result from coupling an amine group on the linker to a carboxylic acid group on the dye. Dyes contemplated in some preferred embodiments include rhodamine dyes, boron dipyrromethene dyes, and cyanine dyes.

Sequencing methods using magnifying tags are described in U.S. Pat. No. 6,723,513, hereby incorporated by reference. The method correlated the relationship between a target nucleic acid and its design polymer counterpart that, for example, may consist of 48 code units of 10 base pairs each. In this example, every base in the target nucleic acid is represented by two binary code units in the design polymer molecule. The A's have been converted to "0" and "0", C's to "0" and "1", G's to "1" and "0" and T's to "1" and "1". The original sequence information found in a target nucleic acid has been maintained in a new and synthetic nucleic acid: a design polymer of 480 base pairs. In preferred embodiments, the conversion of a 24-base pair target nucleic acid is initiated by a class IIS restriction enzyme that cleaves off the two first bases to be converted. These two bases are then identified with a ligase dependent recognition system and replaced with four code units of design polymer that represent the information of the two target bases. The design polymer block with code units are then attached to the target nucleic acid on the opposite side of where the two first bases were initially removed, allowing the process to be repeated with the next two bases in the target nucleic acid. The process is repeated thus building up a design polymer of 48 units representing the original target nucleic acid sequence of 24 base pairs.

EXAMPLES

Example 1

Detection of Changes in the End-to-End Distances of Single Nucleic Fragments Undergoing Polymerization by Polymerase The total number of bases in a given nucleic acid (e.g., DNA) molecule undergoing polymerization is distributed between single-stranded (ss) and double-stranded (ds) forms (FIG. 1). The distribution changes as the polymerase moves along the ss. The end-to-end distance of the dsDNA-ssDNA construct (i.e. single-stranded part plus double-stranded part) changes according to the progress of the reaction:

$$n_{dsDNA} - m_{ssDNA} + k\, dNTP \rightarrow (n+k)_{dsDNA} - (m-k)_{ssDNA}$$

Figure 2:
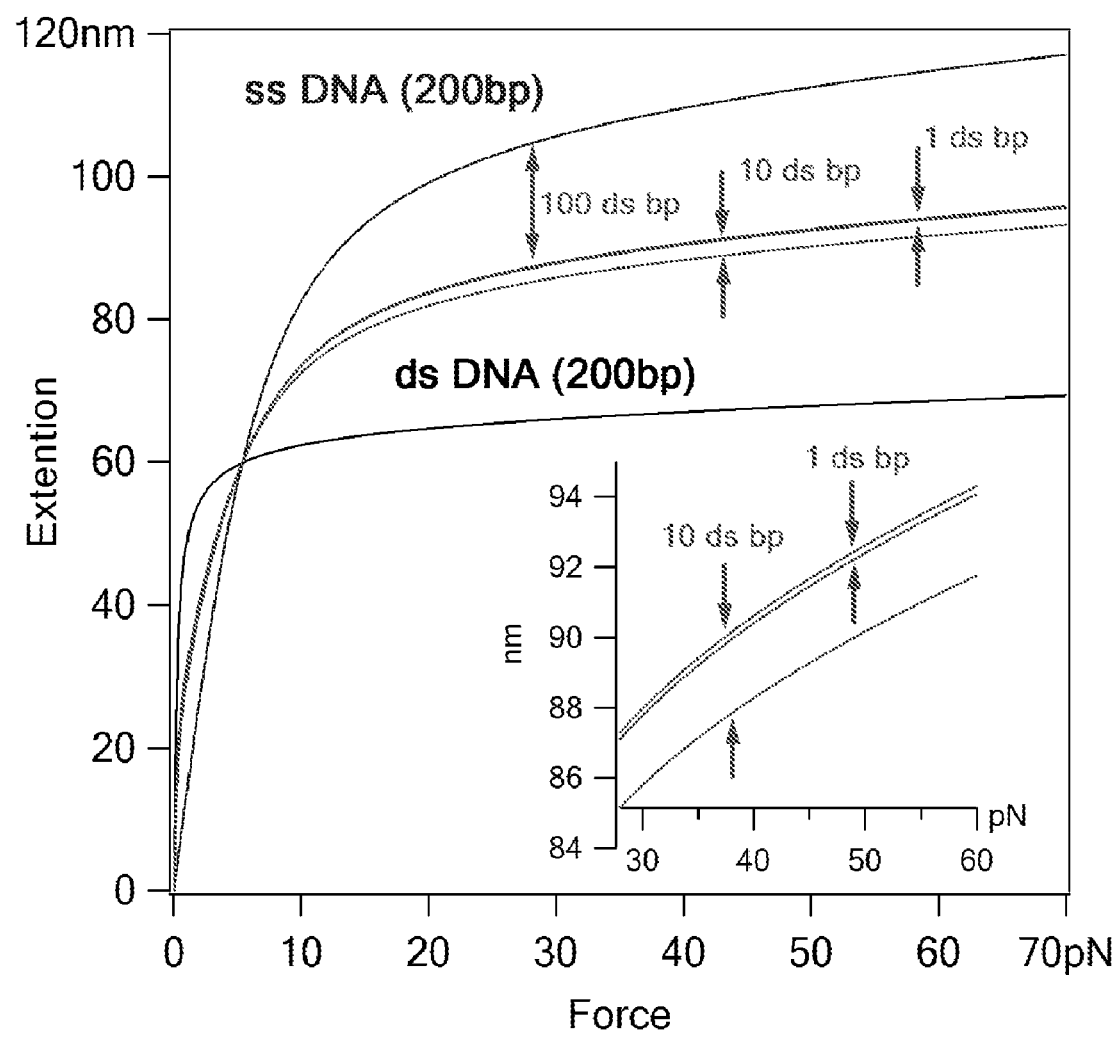
FIG. 2 shows a force-extension diagram for 200-mer undergoing change from ss form (blue curve) to ds form (black). Intermediate stages (red) corresponding to 100 ds bp, 101 ds bp, and 110 bps re also shown.

FIG. 2 shows theoretical predictions of the response of the dsDNA-ssDNA construct to external force. From the simulation data presented in the FIG. 2, one can identify approaches to implement the detection of the extent of polymerization, i.e., i) to observe the free end of the nucleic acid under constant force (e.g. no force or F ~30 pN), or ii) to acquire a full force-extension curve over a 50 pN range. In the first approach, one should determine the position of a centroid of the fluctuating end; in the second case, one provides a fitting routine describing molecular elasticity in order to average out the noise of thermal fluctuations.

Figure 3:
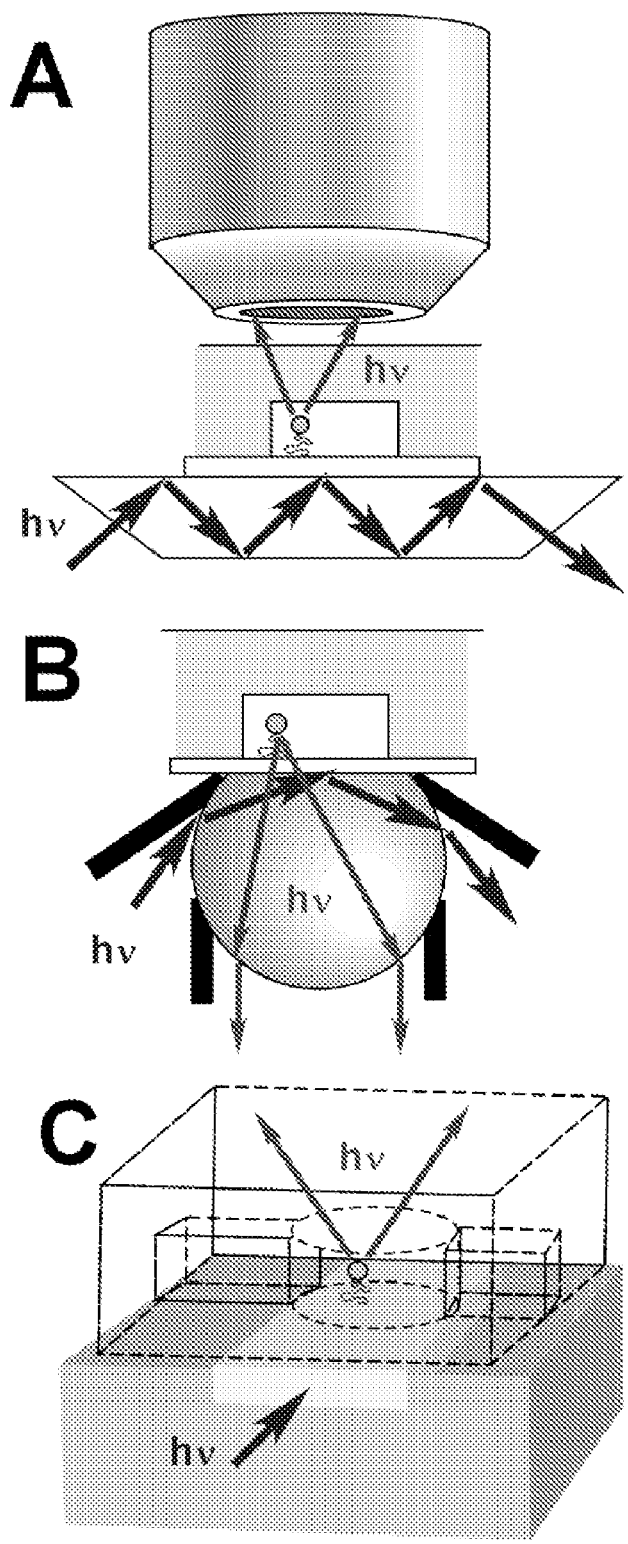
FIG. 3 illustrates embodiments for excitation of near-field probes by the evanescent field: TIR microscopy using prism (A) or objective (B) illumination; and (C) use of slab waveguides for the excitation of the probes positioned within the evanescent field in the cladding of the waveguide.

One detects differences in the averaged response before and after addition of the solution of dNTP to decide whether the base addition has happened. The detection of changes in the end-to-end distances of single nucleic fragments undergoing polymerization via SNA by polymerase is a genome sequencing method that does not require fluorescently labeled dNTPs. For the detection of the distance between the free end and the surface, one may use an optical evanescent field in the vicinity of the glass-aqueous solution interface. One may generate such optical near-fields using total internal reflection (TIR) configuration for the illumination of the glass-solution interface (FIG. 3). In addition to the near-field optical probes reporting end-to-end distances of DNA fragments, one may use magnetic probes as i) either part of the optical probe (for instance by doping dielectric spheres with ferro- and superparamagnetic nanoparticles), or ii) in tandem with near-field probes to pull on individual nucleic acid fragments. One may use magnetic handles to provide for uniform application of external force using permanent magnets or electromagnets (FIG. 4).

Example 2

Detecting Distance of Near-Field Probe from Surface

The sensitivity of the method in detecting the distances from the interface has been demonstrated in the following experiment, performed on a model system. We prepared a polymer sample (polymethylmethacrylate, PMMA) that had steps of increasing depth: 50, 100, 150, and 200 nm. These steps were then covered by a thin polymer film (collodion) that served as a cover slip in conventional oil immersion microscopy. We imaged these steps using a high numerical aperture objective (N.A.=1.4). Because of the varying air gap thickness between the two dielectrics, the TIR was "frustrated" by a different amount and the image intensity reflects different amounts of light totally reflected at the polymer-air TIR interface. From this data, one can clearly distinguish positions of the dielectric surfaces at 50 nm and 100 nm distances away from the cover slip, i.e. exactly within the range of distances expected of the transformation for a 200-mer between the single-stranded and double-stranded forms.

One may use electron multiplying CCD cameras capable of single photon detection to provide imaging with the sub-nm precisions for detection of SNA through corresponding shifts in the position of the optical probe.

One may observe arrays of single DNA fragments on the surface with several configurations of the optical near-field (FIG. 3): i) dove prism with observation of the scattered or fluorescent light using the compound microscope (use of low NA objectives is possible in this case); ii) TIR microscope with the same objective used for illumination and observation (illumination is done using marginal rays of the objective); iii) evanescent field of the cladding using slab waveguides and iv) evanescent field in subwavelength aperature (zero mode waveguide, see FIG. 14). The experimental configuration involving a TIR microscope is preferable because it ensures the high degree of flexibility in the manipulation of the parameters of the evanescent field (intensity, angle of incidence, penetration depth, wavelength, etc.), ease of observation of the surface attached single molecules, and provides access (from the top) to reaction chambers for further manipulation.

Wide field microscopy allows one to simultaneously analyze multiple single DNA fragments. With a field of view for high NA objective on the order of 100 µm×100 µm, at least $10^4$ molecules can be arranged in a single reaction chamber (with ~1 µm average spacing between nearest neighbors). For a typical 1 megapixel CCD, a single optical probe is imaged on 10×10 pixel area, enough for unambiguous identification and tracking of individual probes. An additional 10-20 fold increase in the number of single molecules tracked at the same time can be accomplished by employing CCD chips with high pixel count (~10 Mpixel).

Example 3

Microfluidics for Miniaturization and Automation of the Cycling of the Single Nucleotide Addition Use of a single molecule assay cuts down significantly on the amount of reagents required for sequencing. Given the small surface area of the reaction chamber used for microscopy on the single DNA fragments (~100 µm×100 µm), minimizing the reaction volume is also appropriate. One implements automated delivery of stock dNTP solutions and buffer washes by using microfluidic devices with the basic features outlined in FIG. 6. After preparation of the glass slide that presents surface reactive sites to single-stranded genomic DNA fragments in defined orientations, one positions the glass slide in a microfluidic device and incubates with the DNA solution. After the DNA binding is complete, one flushes the device with buffer and introduces a suspension of near-field probes. Preferably, each of the DNA fragments binds only one such probe, and after incubation with the probes, one flushes the devices with the buffer and prepares them for SNA reactions.

One adds single dNTPs to the reaction in limiting amounts together with polymerase. Upon addition of the complementary dNTP, the DNA polymerase extends the primer and pauses when it encounters a noncomplementary base. After washing, one measures elongation of the single DNA strands and records and adds a different dNTP. One reiterates DNA synthesis and a new cycle begins. One pauses the reaction by closing the inlet/outlet valves in the linked array of reaction chambers. One records the state of each reaction chamber as a series of images by scanning the whole chip containing an array of freely arrayed single DNA molecules (within the confinement of each reaction chamber).

Example 4

Attachment of DNA Fragment to Flat Surfaces and Near-Field Probes

One works with a known 200 bp DNA fragment (synthesis) and generates sufficient quantities of it by a PCR reaction. One may use DNA fragments with unknown sequences. One isolates genomic DNA from a common bacterial laboratory strain *Escherichia coli* K-12 whose sequence has been published. One isolates genomic DNA isolated using the DNeasy kit (Qiagen, CA) according to the manufacturer's instruction. One digests the DNA with restriction endonucleases AccII, HaeIII, and Sau3A (New England Biolabs, MA). These endonucleases recognize 4-base pair stretches within the DNA thereby increasing the cutting probability. One tests these enzymes by themselves or in combination to generate a blunt-ended DNA library pool with average lengths between 100-300 base pairs. One obtains a homogeneous population of similar sized fragments digests by separation on 6% PAA gels and extracting and purifying fragments corresponding to 200 bp size over a Qiaquick PCR purification column.

To the blunt-ended double-stranded DNA fragments of the genomic DNA library, one ligates small double-stranded DNA linkers using T4 DNA ligase (New England Biolabs, MA). Two classes of linkers (adaptors) termed "A" and "B" will be used in each reaction (see FIG. 7 and FIG. 8). Adaptor A carries a universal primer recognition site (SP6). Adaptor B carries a 3'-thiol modification site that enables one to purify fragments by S—S bridge formation (negative selection), and a 5' biotin tag that complexes to a paramagnetic streptavidin coated polystyrene bead during the sequencing reaction. Each adaptor pair contains a 5' overhang and a 3' blunt end to ensure directional ligation to the genomic DNA fragment.

A blunt-ended cloning strategy results in three possible ligation events: DNA fragments with flanking A/A, A/B, or B/B linker combinations (see FIG. 8). To specifically enrich for A/B containing single-stranded DNA fragments, one passes the ligated reaction mixture over activated maleimide (Mal) groups that have been immobilized to polystyrene beads. B-fragments containing the SH group bind to the activated Mal-coated beads, one washes away unbound material lacking the SH adaptor. One denatures the immobilized fragments using alkali treatment thereby releasing the A/B fragments that one uses in the subsequent sequencing steps after neutralization and concentration over a MinElute PCR purification column (Qiagen, CA). One assesses the quality and quantity of the resulting ssDNA library with the Agilent 2100 bioanalyzer using an RNA Pico Lab chip. To prepare for the sequencing conditions one hybridizes the ssDNA library molecules onto beads onto which SP6 universal primer that contains a spacer. Subsequently, one incubates the immobilized fragments with paramagnetic Streptavidin beads (Dynal), beads-QD constructs, or iron nanoparticles-QD constructs, all of which one captures by the biotin group introduced with the adaptor B at the 5' end of the ssDNA fragments.

Example 5

Primer Design and Generation of Double-Stranded Linkers

The adaptor pairs are designed to allow directional ligation to the blunt-ended fragmented genomic DNA (Adaptor pair A: 5'-TATAGCATTTAGGTGACACTATAGGC-3'; 5'-GCCTATAGTGTCACCTAAATGC-3' (SP6 primer recognition site underlined); Adaptor pair B: 5'-GCTGACCTAGTCAT-TGCTAGC-(CH2)2-SH-3'; 5'-GCTGACCTAGTCAT-TGCTAGC-(CH2)2-SH-3'). One mixes and places equal volumes of both complementary oligos at equimolar concentrations in a standard heatblock at 90° C. and allows the mixture to cool to room temperature within 45 to 60 minutes. One captures eluted single-stranded DNA fragments at their 5' ends by binding to SP6 oligonucleotides (5'-NH2-(CH2)6-TACGATTTAGGTGACACTATAG-3) that have been covalently bound to the sequencing chamber surface via a reactive amino group.

It is also contemplated that primers may be developed that incorporate desirable sequences into the ends of a nucleic acid during PCR since the primer ends are replicated. Examples such as hairpin loops and polyA tails are illustrated in FIG. 11.

Example 6

Directional Binding of Freely Arrayed DNA Fragments in a Low Density

One captures DNA fragments by complementary binding to SP6 primer oligonucleotides that have been immobilized at low density. To generate surfaces presenting c-SP6 on the amine-terminated surface (via silanization of glass using aminopropyltriethoxysilane), one incubates the sequencing chamber with either of two types of bifunctional PEG linkers—capped with i) either N-hydroxysuccinimyl (NHS) and methoxy (OMe) groups or ii) NHS and Mal groups. One allows the SH coupled c-SP6 oligonucleotides to link to the reactive Mal groups. The covalently bound c-SP6 primer binds and captures the complementary binding site introduced via the A-linker. Alternatively, one directly links the A-linker with a reactive group to enable direct covalent binding of single DNA fragments to the bottom surface of the sequencing chamber. See FIGS. 10 and 11 for alternative examples.

Example 7

Atomic Force Microscope Experiments

The surface of glass presents identical DNA fragments (designed synthetic sequences) terminated in the near-field probe (polystyrene sphere or 4-6 nm CdS quantum dot, FIG. 9). The near-field probe and force microscope probe (AFM tip) have long-chain polymer linkers (polyethylene glycol, or PEG) terminating in the biotin and avidin, respectively. One forms a biotin-avidin bond by sampling the surface of the glass with the AFM tip. One detects bond formation by monitoring the force exerted on the AFM tip. Once non-zero force is detected, one generates FE curves for a single DNA fragment and records the photonic response of the near-field probe. One calibrates the photonic response, because one independently records DNA end-to-end distance in a FE curve obtained with a scanning probe microscope. By changing the nature of the optical probe from dielectric to QD, one compares the sensitivity of the two approaches. Since one uses the same DNA sequence in these model experiments, one records the changes in mechanical properties of the single DNA fragments by repeating force spectroscopy experiments after one or more cycles of dNTP addition and corresponding elongation of the dsDNA part by polymerase. One carries out the polymerization reaction in situ in the liquid cell of the force microscope. One observes change in the fraction of the dsDNA (by 10 or more bp), then decreases the fractional change to a single dNTP addition. To aid the alignment and positioning of the AFM probe, one attaches near-field probes and concurrently observes the sample with light microscopy.

Example 8

Massively Parallel Force Spectroscopy with Magnetic Tweezers

One may use magnetic tweezers for 1) force induced dissociation experiments (on-off binding); 2) extension under constant force with micron sized steps; and 3) rotation of the single molecule (torque application). One translates millimeter level changes in the distance between the magnetic probe and the magnets into picoNewton changes in force, and translates changes in intensity of the optical signal form the near-field probes (scattered light or fluorescence) into sub-nm changes in the length of the molecules.

One may also use iron ferromagnetic nanoparticles as magnetic probes in tandem with QDs as near-field probes. Methods for the synthesis of fully dispersed nanoscale iron particles are disclosed in Zhang (2003) Journal of Nanoparticle Research 5, 323-332. The particles have sizes in the range of 6-8 nm. Smaller particles of 2-4 nm have also been prepared with a similar method.

Iron nanoparticles were prepared by mixing equal volumes of 0.94 M NaBH$_4$ and 0.18 M FeCl$_3$. The borohydride solution was slowly added into the iron chloride solution with vigorous stirring (400 rpm). Polyvinyl alcohol-co-vinyl acetate-co-itaconic acid (PV3A, Aldrich) was identified as the most promising substrate for the stabilization of iron nanoparticles. Furthermore, PV3A is nontoxic and, thus, compatible with health related applications. PV3A possesses multiple functional groups including hydroxyl (—OH), carbonyl (—C=O), and carboxylic acid (—COOH).

One obtains the estimate of the rate of sequencing with parallel FS setup by assuming that a single FE experiment on a 100×100 array can take 1 sec (e.g., FE curve with 30 data points derived from 30 frames taken at the standard 30 Hz video rate). If the exchange of dNTP buffer in the microfluidic device takes another 1-3 seconds, the maximum rate of ~10,000 bp/4 sec=500 bp/sec (1 base out of 4 is added on average). One boosts this rate further by scanning an array of reaction chambers (thus making reaction time less important). A pathway to a several orders of magnitude increase in speed lies in increasing the field of view and the resolution of the imaging CCD. For example, a 1000×1000 array with a 10 megapixel CCD increases the rate for a single chamber to ~50,000 bp/sec. In addition, the instrument does not have to rely on scanning multiple reaction chambers by a single objective CCD: an array of chambers each having a dedicated solid immersion lens (i.e. an objective directly fused into the surface of the chamber) projects a magnified image of each reaction chamber on individual CCD imagers, recording SNA reactions on all single DNA fragments at the same time.

Example 9

Hybridization of 8-mer Segments to a DNA Array

Figure 5:
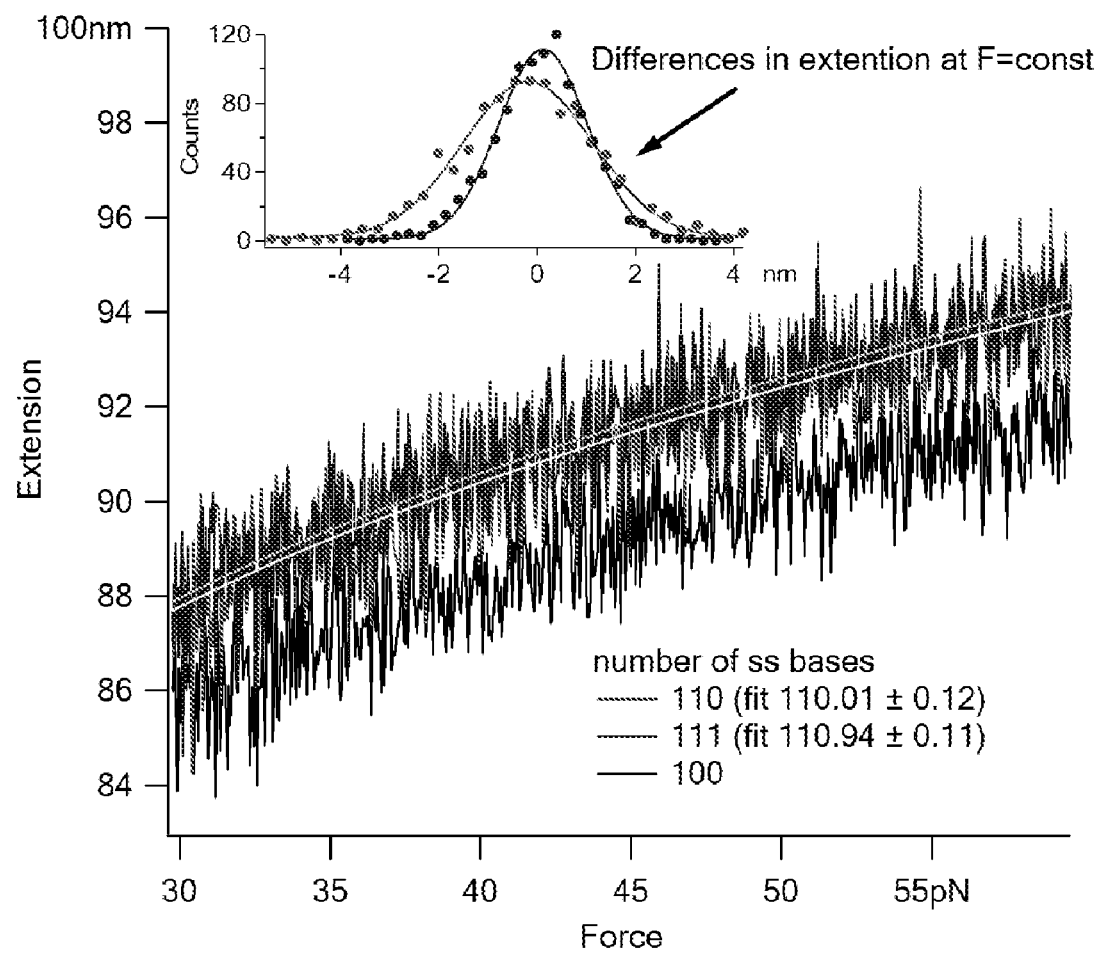
FIG. 5 shows FE curves for 200-mer with 100, 110, 111 single-stranded bases (the rest are ds) and illustrates the ability to resolve the change in two force-extension curves where differences are an order of magnitude smaller than the expected noise level. Curves in the figure noiseless curves in the insert of FIG. 2.

To simulate thermal noise, the random Gaussian noise with standard deviation $$\sqrt{\langle x^2 \rangle} = \sqrt{k_B T / k_{molec}}$$

was added to theoretical curves on extension vs. applied force ($k_{molec}$ is the stiffness of the DNA molecule). The traces in FIG. 5 show FE curves for 200-mer with 100, 110, 111 single-stranded bases (the rest are ds). The signal for SNA is swamped by noise; however, further analysis shows that it is recoverable if data is reproducible. Two methods are suggested in the figure: i) subtracting the two curves (with 110 and 111 ss) and then comparing the averages (avg=0 for no SNA addition—red curve, avg~0.19 nm for SNA—blue curve), or ii) fitting the FE curves to theoretical models setting the number of ss bases as a fit parameter (the two fits differ by 0.93±0.23~1 base). Thus, in spite of the noise level being on the order of 4 nm, the average change in the elastic response is detectable.

Further, from the simulation one sees that the addition of >5 bases can be detected even without special care devoted to noise. This observation leads to an alternative approach of DNA sequencing that uses the same force spectroscopy platform. One may use hybridization of unique 8-mer segments to a DNA array. The detection requirements are then much less stringent, but at the expense of having $4^8$~65000 stock solutions instead of only 4 solution of the dNTPs.

Example 10

Generation of Hetero-Bifunctionally Labeled DNA Fragments from Lambda DNA as a Model System Fragments of Lambda DNA were made by sonication, and sizes of approximately 500 bp were selected by PAGE. The selected fragments were "end-repaired" and then ligated to a bifunctional adapter (carrying an amino- and a sulfhydryl group). The ligated DNA was separated from unincorporated adapter by PAGE, eluted and used directly to bind the DNA fragment to a glass surface.

Sonication was done on ice in continuous 10 sec pulses at 5 W output and analyzed on a 3% agarose gel. With increasing number of pulses (1×, 3×, or 5×), the Lambda DNA was disrupted into shorter fragments.

The End-Repair Kit™ by EpiCentre was used to "blunt" and phosphorylate the ends of the fragments and the prepared fragments (selected to be about 400 bp in length) were incubated with ligase and the adapter.

The adapter was prepared by mixing equimolar ratios of 5'-SH-T15-GAGAATGAGGAACCCGGGGCAGTTCCA-3' and 3'-NH2-A5-CTCTTCCTCCTTGGGCCCCGT-CAAGGT-5' in an annealing buffer, heating to 80° C. (10 min), then slowly cooling to room temperature. The sequencing primer was 5'-GAGAATGAGGAACCCGGGGCAG-3'.

DNA fragments incubated with ligase resulted in high molecular weight DNA. When the ligation mixture contained a 25 molar excess of the adapter, however, fragments about 500 bp in length resulted, the size shift being attributable to ligation of the adapter.

The invention claimed is:

1. A method of determining the presence of a specific oligonucleotide in a sample comprising:
   (1) providing,
      a) a sample suspected of containing said oligonucleotide,
      b) a substrate,
      c) a first nucleic acid conjugate comprising:
         (i) at least a portion of a single-stranded nucleic acid, said portion having a first end and a second end and further comprising a nucleotide sequence complementary to said oligonucleotide, wherein said first end of said single-stranded portion is immobilized on said substrate,
         (ii) a distance marker, and
         (iii) a molecular handle,
      wherein said second end of said single-stranded portion is linked to said distance marker and to said molecular handle,
      d) an instrument configured to (i) exert a stretching force on said molecular handle, (ii) measure said force and (iii) measure a change in a distance between said substrate and said distance marker;
   (2) moving said molecular handle with said instrument under conditions such that said single-stranded nucleic acid is stretched,
   (3) measuring a first change in said distance between said substrate and said distance marker and said force associated therewith under the conditions defined in step (2),
   (4) contacting said sample and said nucleic acid conjugate under conditions such that said oligonucleotide hybridizes to said nucleic acid conjugate to create a second nucleic acid conjugate such that at least a portion of said second conjugate is a double-stranded nucleic acid,
   (5) moving said molecular handle with said instrument under conditions such that said double-stranded nucleic acid is stretched,
   (6) measuring a second change in said distance between said substrate and said distance marker and said force associated therewith under the conditions defined in step (5), and
   (7) correlating said measured forces and changes in distances to a presence of said oligonucleotide in said sample.

2. A method comprising:
A) providing
   (1) a system for stretching a nucleic acid, said system comprising
      a) a substrate,
      b) a nucleic acid conjugate comprising
         (i) a single-stranded nucleic acid having a first end and a second end, wherein said first end is immobilized on said substrate,
         (ii) a nucleotide sequence complementary to said single-stranded nucleic acid and hybridized thereto to create a partially double-stranded nucleic acid, wherein said complementary sequence has a free 3' end,
         (iii) a distance marker, and
         (iv) a molecular handle,
      wherein said second end of said single-strand is linked to said distance marker and to said molecular handle,
      c) an instrument configured to (i) exert a stretching force on said molecular handle, (ii) measure said force and (iii) measure a change in a distance between said substrate and said distance marker;

(2) a sample comprising a nucleotide,
B) moving said molecular handle with said instrument under conditions such that said partially double-stranded nucleic acid is stretched,
C) measuring a first change in said distance between said substrate and said distance marker and said force associated therewith under the conditions defined in step B),
D) contacting said sample and said conjugate under conditions such that said nucleotide is ligated to said free 3' end of said complementary sequence to create an extended double-stranded nucleic acid,
E) moving said molecular handle with said instrument under conditions such that said extended nucleic acid is stretched,
F) measuring a second change in said distance between said substrate and said distance marker and said force associated therewith under the conditions defined in step E, and,
G) correlating said measured forces and changes in distances to a presence of a complementary nucleotide in said nucleic acid.

3. The method of claim 2, further comprising repeating steps D-G to determine the sequence of said nucleic acid.

4. The method of claim 2, wherein said distance marker is selected from the group consisting of a luminescent moiety, a dielectric sphere, and a metallic particle.

5. The method of claim 4, wherein said luminescent moiety is a quantum dot.

6. The method of claim 2, wherein said molecular handle is selected from the group consisting of a ligand, a magnetic particle, and a particle of a size between $1 \times 10^{-9}$ m to $10^{-4}$ m.

7. The method of claim 2, wherein said instrument comprises a proximity probe comprising a receptor.

8. The method of claim 7, wherein said probe is a cantilever tip.

9. The method of claim 7, wherein said receptor is streptavidin.

10. The method of claim 2, wherein said instrument comprises a magnet.

11. The method of claim 2, wherein said instrument is configured to create an optical trap.

12. The method of claim 2 wherein steps B and E are repeated over a range of forces and stretch distances to create data and said data are correlated to determine F) correlating said data to determine the sequence of said nucleic acid.

13. The method of claim 12, further comprising the step of removing the thermal noise by averaging said data or by averaging differences between two sets of said force-length data.

14. The method of claim 12, further comprising the step of removing the effect of said noise by fitting the averaged or individual force-length data measurements to a model of a stretched polymer chain.

15. A method comprising:
A) providing
(1) a system for stretching a nucleic acid, said system comprising:
a) a substrate
b) a nucleic acid conjugate comprising
(i) a single-stranded nucleic acid having a first end and a second end, wherein said first end is immobilized to said substrate substrate,
(ii) a distance marker, and
(iii) a molecular handle;
wherein said second end of said single-strand is linked to said distance marker and to said molecular handle, and
c) an instrument configured to (i) exert a stretching force on said molecular handle, (ii) measure said force and (iii) measure a change in a distance between said substrate and said distance marker;
(2) a plurality of samples, wherein each said sample comprises an oligonucleotide containing at least six contiguous nucleotides, and wherein said samples collectively contain all possible nucleotide sequences in a predetermined set of nucleotides,
(3) moving said molecular handle with said instrument under conditions such that said single-stranded nucleic acid is stretched;
(4) measuring a first change in said distance between said substrate and said distance marker and said force associated therewith under the conditions defined in step (3),
(5) contacting one of said samples and said nucleic acid conjugate under hybridizing conditions for said oligonucleotide in said sample;
(6) moving said molecular handle with said instrument under conditions such that said nucleic acid is stretched;
(7) measuring a second change in said distance between said substrate and said distance marker and said force associated therewith under the conditions defined in step (6);
(8) correlating said first measured change in said distance between said substrate and said distance marker and said force associated therewith and said second measured change in said distance between said substrate and said distance marker and said force associated therewith to determine a presence of a complementary oligonucleotide sequence in said nucleic acid;
(9) repeating steps 5-8 with other of said samples to identify all partial sequences in said single-stranded nucleic acid that hybridize with said complementary oligonucleotides.

* * * * *

SEQUENCE LISTING

<160> NUMBER OF SEQ ID NOS: 9

<210> SEQ ID NO 1
<211> LENGTH: 22
<212> TYPE: DNA
<213> ORGANISM: Artificial Sequence
<220> FEATURE:
<223> OTHER INFORMATION: Synthetic

<400> SEQUENCE: 1
gcctatagtg tcacctaaat gc                                        22

<210> SEQ ID NO 2
<211> LENGTH: 21
<212> TYPE: DNA
<213> ORGANISM: Artificial Sequence
<220> FEATURE:
<223> OTHER INFORMATION: Synthetic

<400> SEQUENCE: 2
gctgacctag tcattgctag c                                         21

<210> SEQ ID NO 3
<211> LENGTH: 21
<212> TYPE: DNA
<213> ORGANISM: Artificial Sequence
<220> FEATURE:
<223> OTHER INFORMATION: Synthetic

<400> SEQUENCE: 3
gctgacctag tcattgctag c                                         21

<210> SEQ ID NO 4
<211> LENGTH: 22
<212> TYPE: DNA
<213> ORGANISM: Artificial Sequence
<220> FEATURE:
<223> OTHER INFORMATION: Synthetic

<400> SEQUENCE: 4
tacgatttag gtgacactat ag                                        22

<210> SEQ ID NO 5
<211> LENGTH: 27
<212> TYPE: DNA
<213> ORGANISM: Artificial Sequence
<220> FEATURE:
<223> OTHER INFORMATION: Synthetic

<400> SEQUENCE: 5
gagaatgagg aacccggggc agttcca                                   27

<210> SEQ ID NO 6
<211> LENGTH: 27
<212> TYPE: DNA
<213> ORGANISM: Artificial Sequence
<220> FEATURE:
<223> OTHER INFORMATION: Synthetic

<400> SEQUENCE: 6
tggaactgcc ccgggttcct ccttctc                                   27

<210> SEQ ID NO 7
<211> LENGTH: 22

-continued

```
<212> TYPE: DNA
<213> ORGANISM: Artificial Sequence
<220> FEATURE:
<223> OTHER INFORMATION: Synthetic

<400> SEQUENCE: 7
gagaatgagg aacccggggc ag                                              22

<210> SEQ ID NO 8
<211> LENGTH: 21
<212> TYPE: DNA
<213> ORGANISM: Artificial Sequence
<220> FEATURE:
<223> OTHER INFORMATION: Synthetic

<400> SEQUENCE: 8
taaaccagtg tgcgcgcgcg g                                               21

<210> SEQ ID NO 9
<211> LENGTH: 13
<212> TYPE: DNA
<213> ORGANISM: Artificial Sequence
<220> FEATURE:
<223> OTHER INFORMATION: Synthetic

<400> SEQUENCE: 9
ggcagcaaaa aat                                                        13
```